US012672761B2

(12) United States Patent
Futami et al.

(10) Patent No.: US 12,672,761 B2
(45) Date of Patent: Jul. 7, 2026

(54) RELAY ADAPTER AND INSERTION INSTRUMENT SYSTEM

(71) Applicant: OLYMPUS MEDICAL SYSTEMS CORP., Tokyo (JP)

(72) Inventors: Shigetoshi Futami, Hachioji (JP); Takahiro Tanabe, Tachikawa (JP); Koji Sakuma, Hino (JP); Takeshi Iga, Hachioji (JP); Jun Konishi, Hachioji (JP); Yoji Sato, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 751 days.

(21) Appl. No.: 18/077,676

(22) Filed: Dec. 8, 2022

(65) Prior Publication Data

US 2023/0181008 A1      Jun. 15, 2023

Related U.S. Application Data

(60) Provisional application No. 63/288,732, filed on Dec. 13, 2021.

(51) Int. Cl.
*A61B 1/00*          (2006.01)
*A61B 1/07*          (2006.01)

(52) U.S. Cl.
CPC ...... *A61B 1/00124* (2013.01); *A61B 1/00103* (2013.01); *A61B 1/00114* (2013.01);
(Continued)

(58) Field of Classification Search
CPC ............ A61B 1/00124; A61B 1/00103; A61B 1/00114; A61B 1/00126; A61B 1/07;
(Continued)

(56) References Cited

U.S. PATENT DOCUMENTS

2009/0209818 A1      8/2009   Higuchi
2016/0249908 A1*    9/2016   Shelton, IV .............. H02J 7/00
                                                        227/175.1
(Continued)

FOREIGN PATENT DOCUMENTS

CN          112312821  A       2/2021
JP          H06-245901 A       9/1994
(Continued)

OTHER PUBLICATIONS

Office Action dated Jul. 28, 2025, issued in corresponding Chinese Patent Application No. 202211579452.0.
(Continued)

*Primary Examiner* — Nasim N Nirjhar
(74) *Attorney, Agent, or Firm* — Morgan, Lewis & Bockius LLP

(57)          ABSTRACT

A relay adapter includes a first connector configured to connect to a processor supplying a first power. The relay adapter includes a second connector configured to connect to an insertion instrument operable using a second power. The relay adapter includes a power circuit coupled to the first connector to receive the first power. The power circuit is configured to convert the first power into the second power. The power circuit is coupled to the second connector for delivering the second power to the second connector. The relay adapter includes a switching circuit coupled to the power circuit. When the second connector is not connected to the insertion instrument, the switching circuit prevents the power circuit from delivering the second power to the second connector.

17 Claims, 16 Drawing Sheets

(52) U.S. Cl.
CPC ............ *A61B 1/00126* (2013.01); *A61B 1/07* (2013.01); *A61B 1/00009* (2013.01); *A61B 1/00029* (2013.01); *A61B 1/00117* (2013.01)

(58) Field of Classification Search
CPC ............ A61B 1/00009; A61B 1/00029; A61B 1/00117; A61B 1/00006; A61B 1/00027; A61B 1/045; A61B 1/0655; A61B 1/00025; A61B 1/00064; A61B 1/00131; A61B 1/0051; A61B 1/015; A61B 1/04; A61B 1/0661; A61B 1/0684
See application file for complete search history.

(56) References Cited

U.S. PATENT DOCUMENTS

| | | |
|---|---|---|
| 2019/0356839 A1 | 11/2019 | Kuhn et al. |
| 2022/0409015 A1 | 12/2022 | Mizoguchi |

FOREIGN PATENT DOCUMENTS

| | | | | |
|---|---|---|---|---|
| JP | H07-000360 A | 1/1995 | | |
| JP | H07-171089 A | 7/1995 | | |
| JP | H07-313454 A | 12/1995 | | |
| JP | H08-122654 A | 5/1996 | | |
| JP | 2002-233500 A | 8/2002 | | |
| JP | 2004-236738 A | 8/2004 | | |
| JP | 2006-034573 A | 2/2006 | | |
| JP | 2007-295980 A | 11/2007 | | |
| JP | 2008-245934 A | 10/2008 | | |
| JP | 2009-189529 A | 8/2009 | | |
| JP | 2009-201543 A | 9/2009 | | |
| JP | 2013-119011 A | 6/2013 | | |
| JP | 5838082 B2 | 12/2015 | | |
| JP | 6930955 B2 | 9/2021 | | |
| JP | 2021-183166 A | 12/2021 | | |
| KR | 101552050 B1 * | 9/2015 | ............... | A61B 1/04 |
| WO | WO-2020080431 A1 * | 4/2020 | ......... | A61B 1/00124 |
| WO | 2021/171427 A1 | 2/2021 | | |

OTHER PUBLICATIONS

Office Action dated May 26, 2026, issued in corresponding Japanese Patent Application No. 2022-198024.

* cited by examiner

| | CONNECTION STATE | CONNECTION DETECTION | POWER INPUT |
|---|---|---|---|
| A | 5 ADAPTER VIDEO PROCESSOR 3  2 | YES | YES |
| B | 5 ADAPTER ↔ VIDEO PROCESSOR 3  2 | NO | NO |

RELAY ADAPTER AND INSERTION INSTRUMENT SYSTEM

RELATED APPLICATION DATA

This application is based on and claims priority under 35 U.S.C. § 119 to U.S. Provisional Application No. 63/288, 732 filed on Dec. 13, 2021, the entire contents of which are incorporated herein by reference.

FIELD OF THE DISCLOSURE

The present disclosure relates to a relay adapter and an insertion instrument system that allow an insertion instrument to be connectable to a processor.

BACKGROUND

Some endoscopes are reusable endoscopes (also referred to as endoscopes for reuse) that are reused by undergoing reprocessing. Some other endoscopes are single-use endoscopes (also referred to as endoscopes for single-use) that are disposed of after being used once.

A connector (single-touch plug) for a reusable endoscope is equipped with an electric circuit board inside the endoscope. The electric circuit board converts a signal format into a format used by a video processor.

When a single-use endoscope is connected to a video processor for a reusable endoscope, the signal format may be converted into a signal format that is processable by the video processor.

A relay cable can be used for allowing a single-use endoscope to be usable by being connected to a video processor for a reusable endoscope.

For example, Japanese Patent Application Laid-Open Publication No. 2021-183166 describes a relay adapter that connects a video processor and an endoscope apparatus. The relay adapter includes an image pickup interface circuit that converts a format of a video signal. In response to instructions from a control portion, the image pickup interface circuit converts a video signal received from an image sensor of the endoscope apparatus into a signal in a format that is processable by the video processor. The image pickup interface circuit produces a signal in the converted format and outputs the converted signal to the video processor.

SUMMARY OF THE DISCLOSURE

A relay adapter includes a first connector configured to connect to a processor supplying a first power. The relay adapter includes a second connector configured to connect to an insertion instrument operable using a second power. The relay adapter includes a power circuit coupled to the first connector to receive the first power. The power circuit is configured to convert the first power into the second power. The power circuit is coupled to the second connector for delivering the second power to the second connector. The relay adapter includes a switching circuit coupled to the power circuit. When the second connector is not connected to the insertion instrument, the switching circuit prevents the power circuit from delivering the second power to the second connector.

An insertion instrument system includes an insertion instrument configured to be inserted into a subject, and a relay adapter. The relay adapter includes a first connector configured to connect to a processor supplying a first power. The relay adapter includes a second connector configured to connect to the insertion instrument, the insertion instrument operable using a second power. The relay adapter includes a power circuit coupled to the first connector to receive the first power. The power circuit is configured to convert the first power into the second power. The power circuit is coupled to the second connector for delivering the second power to the insertion instrument via the second connector. The relay adapter includes a switching circuit coupled to the power circuit. When the second connector is not connected to the insertion instrument, the switching circuit prevents the power circuit from delivering the second power to the second connector.

DETAILED DESCRIPTION

Figure 1:
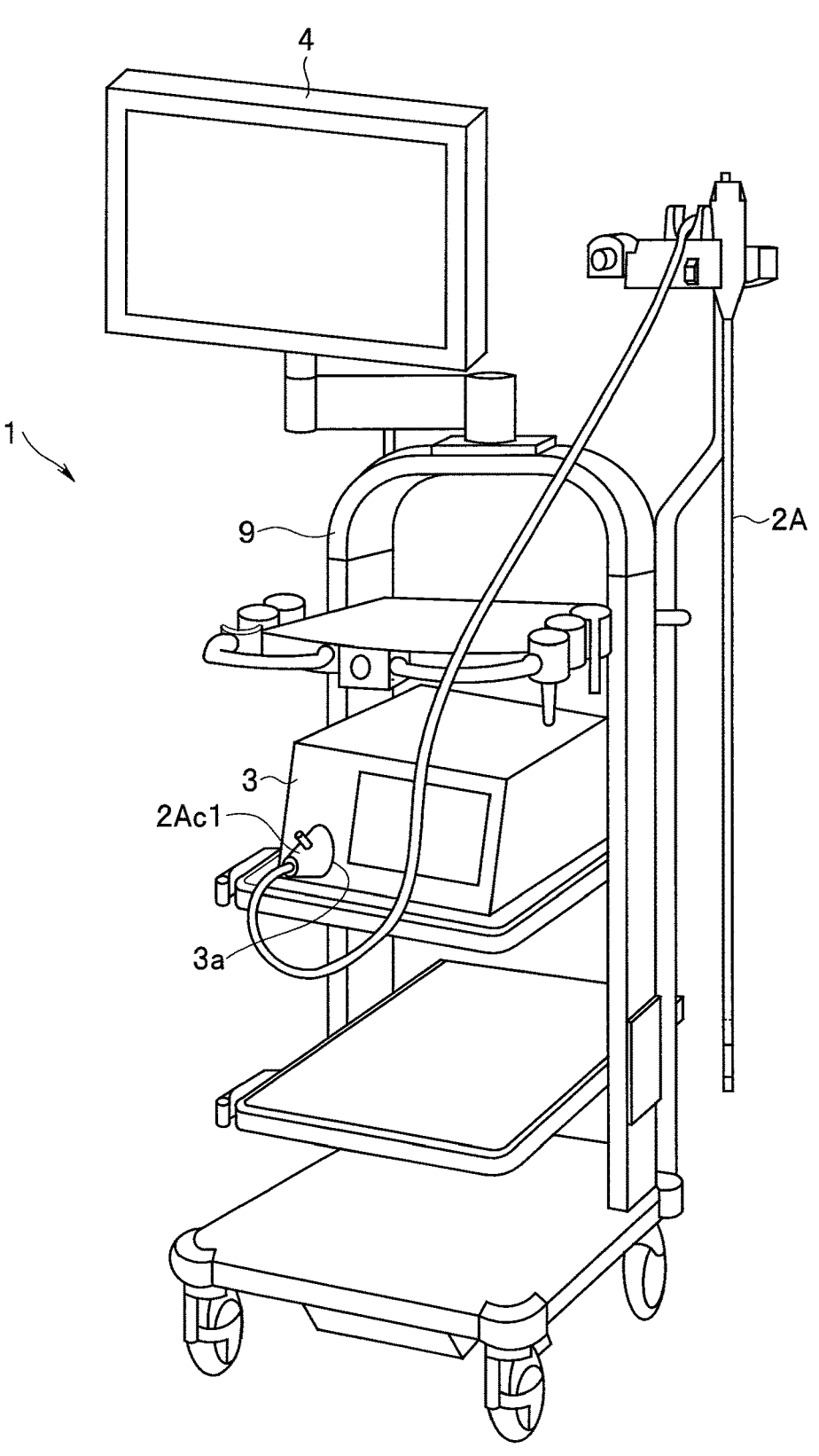
FIG. 1 is a perspective view showing an endoscope system configured with a reusable endoscope in a first embodiment of the present disclosure.

Hereinafter, embodiments of the present disclosure will be described with reference to the drawings. However, the present invention is not limited to the embodiments described below.

Note that the same or corresponding elements are appropriately assigned the same reference numerals in the drawings. The drawings are schematic, and the relation in length among the elements, the ratio in length among the elements, the number of the elements, and the like within a single drawing may be different from the actual relation, ratio, number, and the like, in some cases, for simplifying the description. Some portions having relations and ratios in length differing among the drawings may also be included.

First Embodiment

FIG. 1 to FIG. 8 show a first embodiment of the present disclosure. FIG. 1 is a perspective view showing an endoscope system 1 configured with a reusable endoscope 2A in the first embodiment.

The endoscope system 1 includes, for example, the reusable endoscope 2A, a video processor 3 (processor), and a monitor 4. The video processor 3 and the monitor 4 are placed on a cart 9 or fixed to the cart 9, as shown in FIG. 1. The reusable endoscope 2A may be hung on a hook of the cart 9 when the reusable endoscope 2A is not in use. The endoscope system 1 is disposed, for example, in an examination room where a subject is examined or treated.

The video processor 3 supplies power to the reusable endoscope 2A and receives an electric signal from the reusable endoscope 2A. In an example shown in FIG. 1, the video processor 3 is a video processor with a built-in light source (light source built-in type video processor) and supplies illumination light to the reusable endoscope 2A. However, as will be described later with reference to FIG. 11 in a fourth embodiment, the video processor 3 may be a body separate from a light source device.

Figure 2:
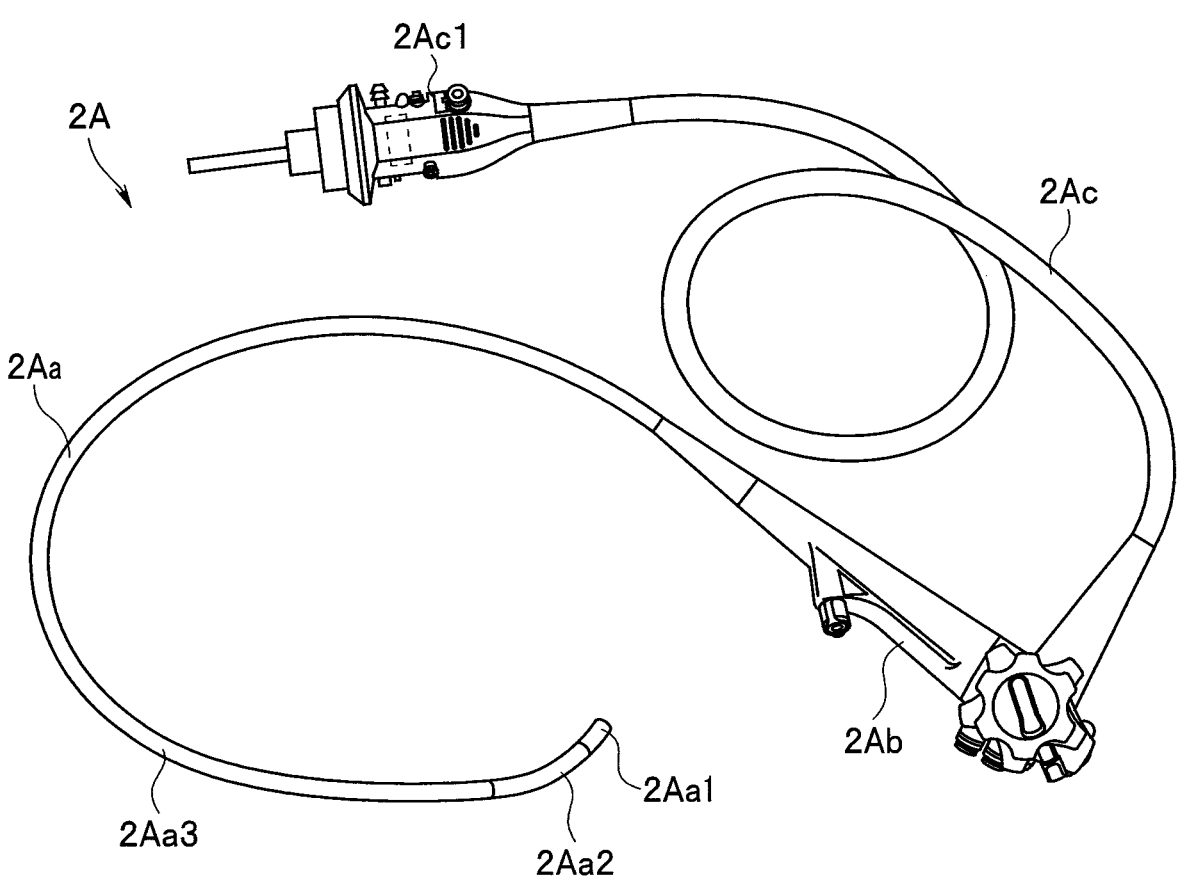
FIG. 2 is a perspective view showing the reusable endoscope of the aforementioned first embodiment.

FIG. 2 is a perspective view showing the reusable endoscope 2A of the first embodiment.

The reusable endoscope 2A is an insertion instrument including a portion to be inserted into a subject. The reusable endoscope 2A is usable multiple times by undergoing reprocessing. The reusable endoscope 2A includes an insertion portion 2Aa, an operation portion 2Ab, and a universal cable 2Ac. The reusable endoscope 2A is configured as, for example, an electronic endoscope.

The insertion portion 2Aa is a portion to be inserted into a subject. For example, a lumen of a living body such as a human or an animal is considered to be the subject. The subject may be a non-living body such as a machine and a building. The insertion portion 2Aa includes a distal end portion 2Aa1, a bending portion 2Aa2, and a flexible tube portion 2Aa3 in this order from the distal end side toward the proximal end side.

An image pickup unit, a distal end portion of a light guide (LG), a distal end side opening of a treatment instrument channel, and the like are disposed in the distal end portion 2Aa1. The image pickup unit includes an image pickup optical system and an image sensor. The image pickup optical system forms an optical image of a subject on the image sensor. The image sensor performs photoelectrical conversion (image pickup) on the optical image of the subject to produce a video signal.

The operation portion 2Ab is disposed on the proximal end side of the insertion portion 2Aa. The operation portion 2Ab is a portion with which a user operates the reusable endoscope 2A.

The universal cable 2Ac extends from, for example, a side face on the proximal end side of the operation portion 2Ab. The universal cable 2Ac is a connection cable for connecting the reusable endoscope 2A with the video processor 3.

A light guide, a signal wire, and an air and water feeding channel are disposed inside the insertion portion 2Aa, the operation portion 2Ab, and the universal cable 2Ac of the reusable endoscope 2A. The treatment instrument channel and a bending operation wire are disposed inside the insertion portion 2Aa and the operation portion 2Ab. A suction channel is disposed inside the universal cable 2Ac and the operation portion 2Ab. The suction channel communicates with the treatment instrument channel inside the operation portion 2Ab.

A connector 2Ac1 (single-touch plug) provided at an extension end of the universal cable 2Ac is connected to the video processor 3. The connector 2Ac1 is equipped with an electric circuit board inside the endoscope that converts the format of a video signal from the image sensor.

For example, the video processor 3 with a built-in light source includes, as a light source, a light emitting device such as an LED (light emitting diode) light source, a laser light source, or a xenon light source. With the connector 2Ac1 connected to the video processor 3, illumination light can be transmitted from the light source to the light guide.

The illumination light from the video processor 3 incident onto the proximal end face of the light guide is transmitted (the light is guided) through the light guide. The transmitted illumination light is emitted from the distal end face of the light guide disposed in the distal end portion 2Aa1 of the insertion portion 2Aa toward a subject.

The video processor 3 transmits a drive signal to drive the image sensor, via the signal wire. The video signal outputted from the image sensor is transmitted via the signal wire, and the signal format is converted by means of the electric circuit board of the connector 2Ac1. The converted video signal is transmitted from the connector 2Ac1 to the video processor 3 via the signal wire.

The video processor 3 performs image processing on the video signal obtained by the image sensor and produces a displayable image signal. The video processor 3 may superimpose character information or the like over the image signal. The video processor 3 outputs the image signal to the monitor 4.

The monitor 4 receives the image signal from the video processor 3 and displays an image including an endoscope image.

Figure 3:
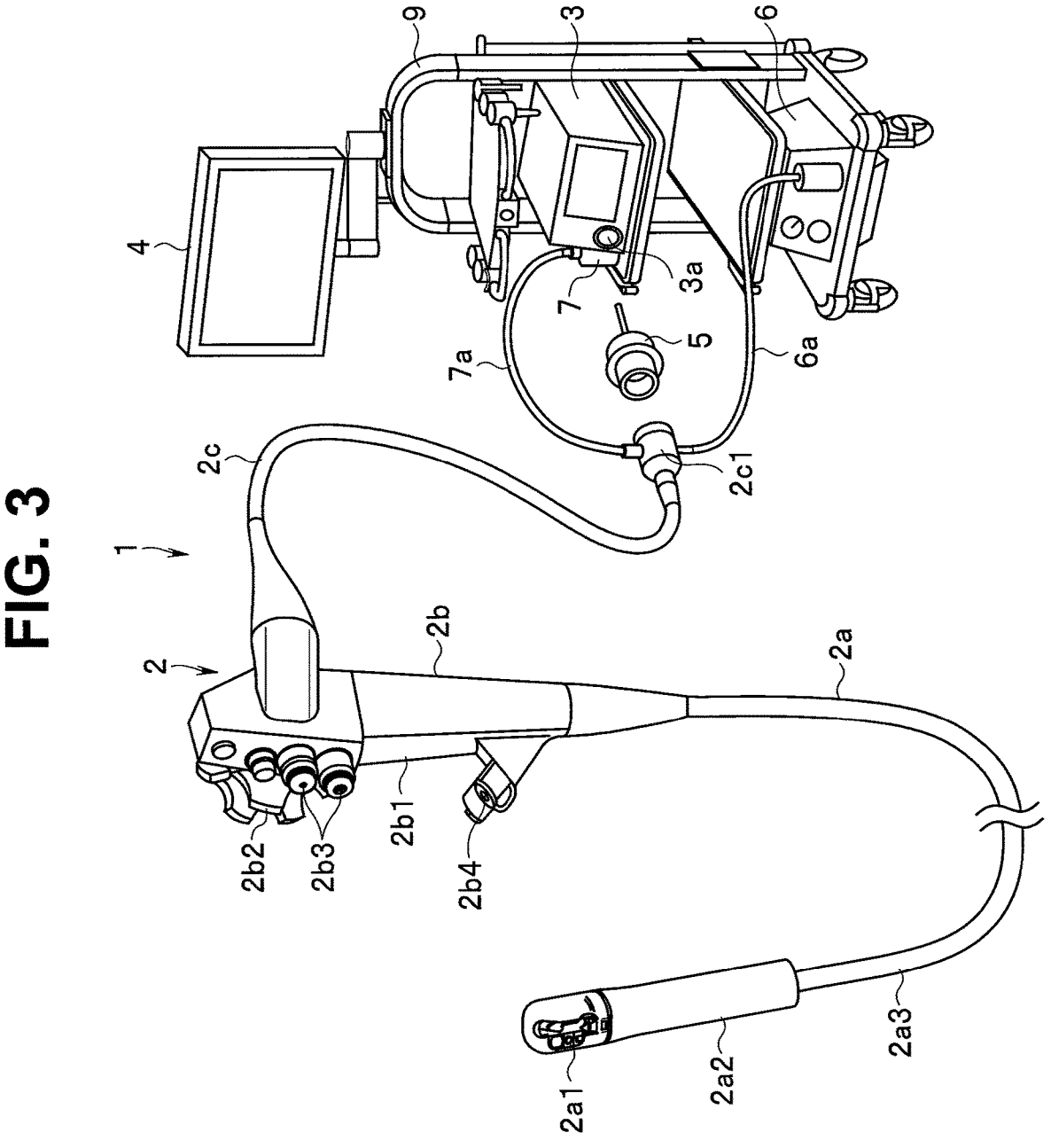
FIG. 3 is a perspective view showing the endoscope system configured with a single-use endoscope in place of the reusable endoscope in the aforementioned first embodiment.

FIG. 3 is a perspective view showing the endoscope system 1 configured with a single-use endoscope 2 in place of the reusable endoscope 2A in the first embodiment.

The endoscope system 1 shown in FIG. 3 includes, for example, the single-use endoscope 2, the video processor 3 (processor), the monitor 4, a relay adapter 5 (hereinafter referred to as the adapter 5), a suction pump 6, and a water feeding tank 7.

The video processor 3 and the monitor 4 are placed on the cart 9 or fixed to the cart 9, as described above. The suction pump 6 is placed on the cart 9 or fixed to the cart 9. The water feeding tank 7 is attached to, for example, a side face of the video processor 3.

The video processor 3, the monitor 4, and the cart 9 are the same as shown in FIG. 1. In other words, the video processor 3 is a processor for a reusable endoscope for use in the reusable endoscope 2A.

Note that although the illustrations are omitted in FIG. 1, the endoscope system 1 using the reusable endoscope 2A may also include the suction pump 6 and the water feeding tank 7.

The single-use endoscope 2 is the insertion instrument including a portion to be inserted into a subject. The single-use endoscope 2 is disposed of after being used once, that is, the single-use endoscope 2 is discarded or collected by a treatment mechanism after being used only once. The single-use endoscope 2 (hereinafter referred to as the endoscope 2 as appropriate) should be used only once, but not multiple times.

The endoscope 2 includes an insertion portion 2a, an operation portion 2b, and a universal cable 2c. The endoscope 2 is configured as, for example, an electronic endoscope.

The insertion portion 2a is a portion to be inserted into a subject. The subject may be either a living body or a non-living body, as described above. The insertion portion 2a includes a distal end portion 2a1, a bending portion 2a2, and a flexible tube portion 2a3 in this order from the distal end side toward the proximal end side.

The image pickup unit, the distal end portion of the light guide, the distal end side opening of the treatment instrument channel, and the like are disposed in the distal end portion 2al. The image pickup unit includes the image pickup optical system and an image sensor 21 (see FIG. 5, etc.). The image pickup optical system forms an optical image of a subject on the image sensor 21. The image sensor 21 performs photoelectric conversion (image pickup) on the optical image of the subject to produce a video signal.

Examples of the image sensor 21 include, but not limited to, a CCD (charge coupled device) image sensor and a CMOS (complementary metal-oxide semiconductor) image sensor.

The bending portion 2a2 is a portion bendable in, for example, two directions or four directions of upward, downward, leftward, and rightward directions.

The flexible tube portion 2a3 is a tube portion having flexibility. Note that the endoscope 2 that is a flexible endoscope having the flexible tube portion 2a3 is provided herein as an example. However, the endoscope 2 may be a rigid endoscope in which a portion corresponding to the flexible tube portion 2a3 is rigid.

The operation portion 2b is a portion with which a user operates the endoscope 2. The operation portion 2b is disposed on the proximal end side of the insertion portion 2a. The operation portion 2b includes a grasping portion 2b1, a bending operation knob 2b2, a plurality of operation buttons 2b3, and a treatment instrument insertion port 2b4.

The grasping portion 2b1 is a portion with which the user grasps the endoscope 2 with the palm.

The bending operation knob 2b2 is an operation device for operating the bending of the bending portion 2a2. The bending operation knob 2b2 is operated using, for example, a thumb of the hand grasping the grasping portion 2b1. When the bending operation knob 2b2 is operated, the bending operation wire is pulled to thus bend the bending portion 2a2.

When the bending portion 2a2 is bent, the direction of the distal end portion 2al changes. Accordingly, the direction in which the image sensor 21 picks up an image and the direction in which the light guide emits illumination light change. The bending portion 2a2 is also bent for improving the insertability of the insertion portion 2a inside a subject.

A plurality of operation buttons 2b3 include, for example, an air and water feeding button, a suction button, and an image pickup-related button. The air and water feeding button is a button to perform air and water feeding to an observation window provided on the distal end face of the image pickup unit in the distal end portion 2al. The observation window is cleaned by feeding a liquid, and the liquid after cleaning is wiped away by feeding air. Air feeding and water feeding are performed via the air and water feeding channel (not shown).

The suction button is a button to perform suction inside a subject through the distal end portion 2a1. Suction inside the subject is performed via the suction channel, for example. When suction is performed, a liquid and a mucosa, for example, are sucked from the inside of the subject.

The image pickup-related button is a button switch to perform a release operation, for example.

The treatment instrument insertion port 2b4 is an opening on the proximal end side of the treatment instrument channel. A treatment instrument such as a forceps is inserted into the treatment instrument channel through the treatment instrument insertion port 2b4. The distal end portion of the treatment instrument projects through an opening on the distal end side of the treatment instrument channel. With the projecting distal end portion of the treatment instrument, various treatments are performed on a subject.

The universal cable 2c extends, for example, from a side face on the proximal end side of the operation portion 2b. A connector 2cl (third connector) is provided at an extension end of the universal cable 2c.

The shape of the connector 2cl of the single-use endoscope 2 differs from the shape of the connector 2Ac1 of the reusable endoscope 2A, for example. Unlike the connector 2Ac1, the connector 2cl does not include the electric circuit board that converts the format of a video signal.

Thus, the single-use endoscope 2 is connected to the video processor 3 via an adapter 5. The video processor 3 supplies power to the endoscope 2 and receives an electric signal from the endoscope 2, via the adapter 5. In other words, the adapter 5 links the video processor 3 and the endoscope 2. The adapter 5 includes a circuit that converts the format of a video signal as will be described later.

Figure 4:
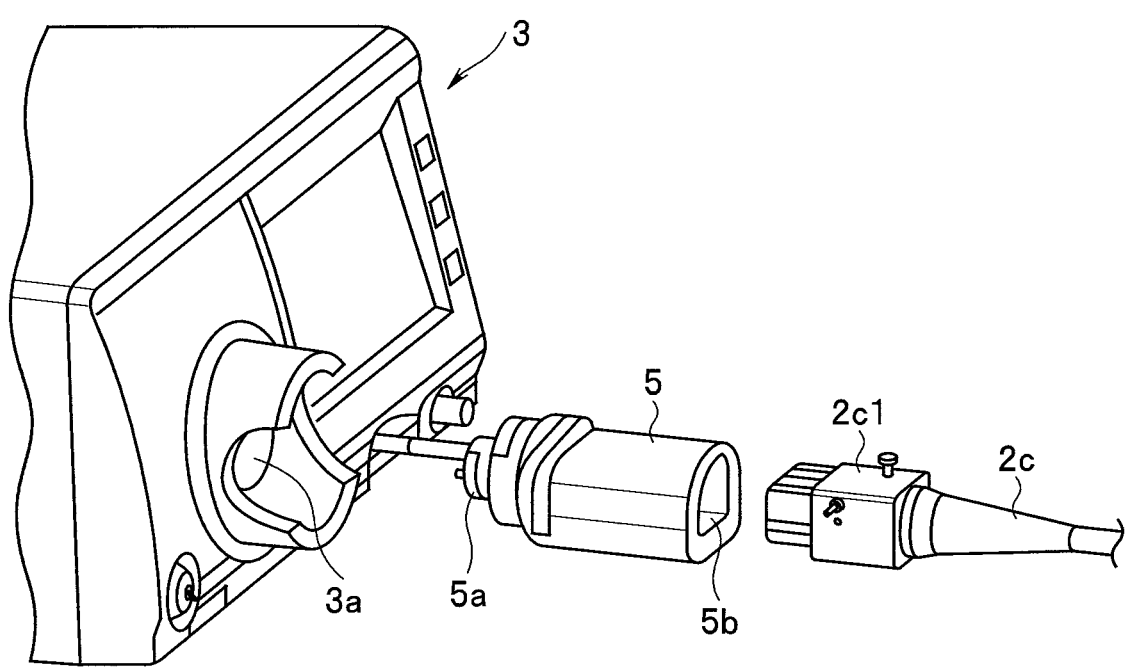
FIG. 4 is a perspective view showing a configuration of a portion where an endoscope and a video processor are connected via an adapter in the aforementioned first embodiment.

FIG. 4 is a perspective view showing a configuration of a portion where the endoscope 2 and the video processor 3 are connected via the adapter 5 in the first embodiment.

The adapter 5 includes, on one end side, a connector receiver 5b (second connector) connected to the connector 2cl of the single-use endoscope 2. The adapter 5 includes, on the other end side, a connector 5a (first connector) connected to a connector receiver 3a of the video processor 3. In other words, the connector 5a (first connector) is configured to be compatible with the connector 2Ac1 of the reusable endoscope 2A. The first connector 5a is configured to connect to the processor 3 supplying a first power, the second connector 5b is configured to connect to the insertion instrument operable using a second power.

The light guide, the signal wire, and the air and water feeding channel are disposed inside the insertion portion 2a, the operation portion 2b, and the universal cable 2c of the endoscope 2. The treatment instrument channel and the bending operation wire are disposed inside the insertion portion 2a and the operation portion 2b. The suction channel is disposed inside the universal cable 2c and the operation portion 2b. The suction channel communicates with the treatment instrument channel inside the operation portion 2b.

For example, the video processor 3 with a built-in light source includes, as a light source, a light emitting device such as an LED (light emitting diode) light source, a laser light source, or a xenon light source, as described above. The adapter 5 includes a light guide and a signal wire. With the connector 2cl connected to the video processor 3 via the adapter 5, illumination light can be transmitted to the endoscope 2.

The illumination light from the video processor 3 is made incident onto the light guide of the endoscope 2 via the adapter 5. The incident illumination light is transmitted to the distal end portion 2al of the insertion portion 2a of the endoscope 2 through the light guide. The transmitted illumination light is emitted from the distal end face of the light guide disposed in the distal end portion 2al toward a subject.

The video processor 3 transmits a drive signal to drive the image sensor 21, via the signal wire of the adapter 5 and the signal wire of the endoscope 2. The video signal outputted from the image sensor 21 is transmitted to the adapter 5 via the signal wire of the endoscope 2.

The adapter 5 performs signal processing on a video signal obtained from the image sensor 21 to convert the video signal into a video signal in a format processable by the video processor 3. The adapter 5 transmits the converted video signal to the video processor 3.

The video processor 3 performs image processing on the received video signal and produces a displayable image signal. The video processor 3 may superimpose character information or the like over the image signal. The video processor 3 outputs the image signal to the monitor 4.

The monitor 4 displays an image including an endoscope image according to the image signal outputted from the video processor 3.

As shown in FIG. 3, the water feeding tank 7 is connected to the connector 2cl of the single-use endoscope 2 by means of an air and water feeding tube 7a. The connector 2cl connects the air and water feeding tube 7a with the air and water feeding channel inside the endoscope 2.

The water feeding tank 7 is a tank for reserving a liquid such as a physiological saline solution. A pressurized air is fed from the air and water feeding pump inside the video processor 3 to the water feeding tank 7, so that the liquid inside the water feeding tank 7 is fed to the air and water feeding channel.

The suction pump 6 is connected to the connector 2cl by means of a suction tube 6a. The connector 2cl connects the suction tube 6a with the suction channel inside the endoscope 2. The suction pump 6 is used for sucking a liquid, a mucosa, or the like from a subject.

The video processor 3 controls the overall endoscope system 1 including the endoscope 2, the suction pump 6, the monitor 4, and the like.

Figure 5:
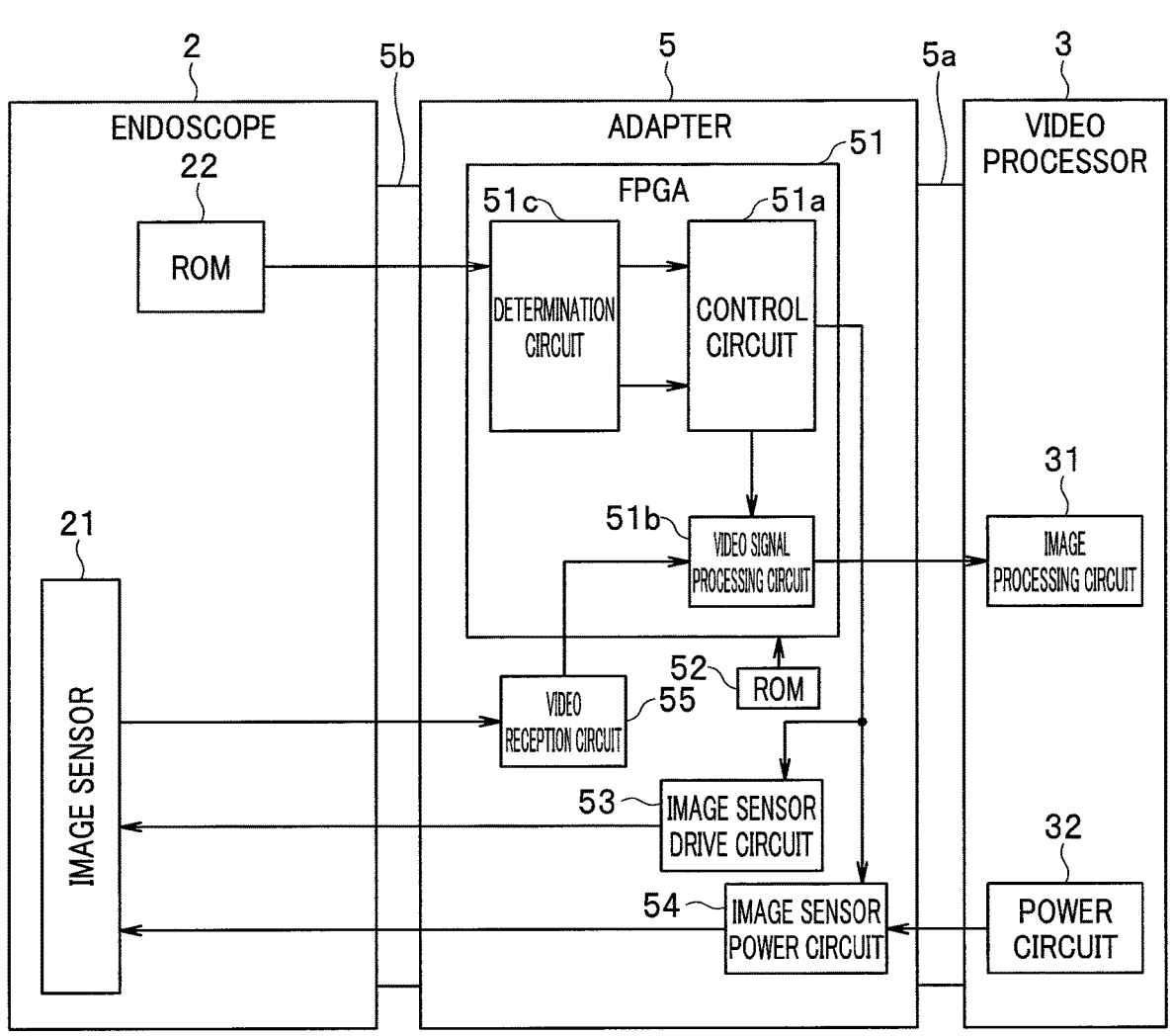
FIG. 5 is a block diagram showing the outline of electric configurations of the endoscope, the adapter, and the video processor in the aforementioned first embodiment.

FIG. 5 is a block diagram showing the outline of electric configurations of the endoscope 2, the adapter 5, and the video processor 3 in the first embodiment.

When the adapter 5 is connected to the video processor 3, the adapter 5 receives power supply from the video processor 3 to be actuated. The endoscope 2 is actuated by receiving the power supply through the adapter 5 connected to the video processor 3.

The endoscope 2 includes an image sensor 21 and a ROM 22 (memory).

The image sensor 21 receives power supply for an image sensor and is driven by an image sensor drive signal. The image sensor 21 is driven to perform image pickup, and then transmits a video signal to the adapter 5.

The ROM 22 stores determination information on the endoscope 2 in a non-volatile manner. The determination information includes model determination information (information on the model of the insertion instrument) and sensor determination information (information on the type of the image sensor included in the insertion instrument). More specifically, the model determination information shows the model information on the endoscope 2 and the sensor determination information shows the type of the image sensor 21. The ROM 22 transmits the determination information to the adapter 5.

The adapter 5 includes a FPGA (field programmable gate array) 51, a ROM 52, an image sensor drive circuit 53, an image sensor power circuit 54 (power circuit), and a video reception circuit 55. The power circuit 54 is directly or indirectly coupled to the first connector 5a to receive the first power, and the power circuit 54 is configured to convert the first power into the second power, and the power circuit 54 is coupled to the second connector 5b for delivering the second power to the second connector 5b.

The ROM 52 is a storage device (memory) that stores processing programs that cause the FPGA 51 to function as various circuits, in a non-volatile manner. The ROM 52 further stores parameters, data, and the like that are used for processing as well in a non-volatile manner.

Note that the FPGA 51 is provided herein as an example of the processor that executes processing, but the processor is not limited to the example and an ASIC (application specific integrated circuit) including a CPU (central processing unit) or the like may be used. The memory is not limited to the ROM 52, but a RAM or the like may further be included. The circuits inside the FPGA 51 or the circuits inside the adapter 5 may partially be configured as dedicated electronic circuits.

The FPGA 51 includes a determination circuit 51c (determination signal receiving circuit), a control circuit 51a, and a video signal processing circuit 51b, as functional circuits.

The determination circuit 51c retrieves determination information by communicating with the ROM 22 inside the endoscope 2. The determination circuit 51c receives, from the ROM 22, a signal (first determination signal related to the model of the insertion instrument) including the information related to the model of the endoscope 2. The determination circuit 51c further receives, from the ROM 22, a signal (second determination signal related to the type of the image sensor included in the insertion instrument) including information related to the type of the image sensor 21 included in the endoscope 2. The determination circuit 51c then determines the model of the endoscope 2 based on the first determination signal and determines the type of the image sensor 21 based on the second determination signal.

At this time, when a first determination signal (model determination information) is not received from the determination circuit 51*c*, the control circuit 51*a* determines that the endoscope 2 is not connected to the adapter 5. In a case where the determination is further precisely made, when the first determination signal (model determination information) and the second determination signal (sensor determination information) are not received from the determination circuit 51*c*, the control circuit 51*a* may determine that the endoscope 2 is not connected to the adapter 5.

When the connector 5*a* and the video processor 3 are connected, but the connector receiver 5*b* and the endoscope 2 are not connected (when the determination circuit 51*c* does not receive the first determination signal), the control circuit 51*a* functions as a switching circuit to cause the image sensor power circuit 54 to shut off supplying power to the endoscope 2. Accordingly, the power supply to the image sensor 21 of the endoscope 2 via the connector receiver 5*b* is not performed. The switching circuit 51*a* is coupled to the power circuit 54 directly or indirectly. When the second connector 5*b* is not connected to the insertion instrument, the switching circuit 51*a* prevents the power circuit 54 from delivering the second power to the second connector 5*b*. When the first connector 5*a* is connected to the processor 3 and the second connector 5*b* is connected to the insertion instrument, the switching circuit 51*a* permits the power circuit 54 to deliver the second power to the second connector 5*b*. The determination signal receiving circuit 51*c* is directly or indirectly coupled via the second connector 5*b* to the insertion instrument to receive a first determination signal from the insertion instrument. The determination signal receiving circuit 51*c* is configured to provide a first output corresponding to receiving the first determination signal and to provide a second output corresponding to not receiving the first determination signal. The determination signal receiving circuit 51*c* is directly or indirectly coupled to the switching circuit 51*a* to deliver the first output and the second output to the switching circuit 51*a*. The switching circuit 51*a* is configured to operate the power circuit 54 to deliver the second power to the second connector 5*b* when the switching circuit 51*a* delivers the first output, and operate the power circuit 54 to prevent delivery of the second power to the second connector when the switching circuit 51*a* delivers the second output. The first determination signal is related to a model of the insertion instrument.

Thus, when the endoscope 2 is not connected, even if the connector receiver 5*b* of the adapter 5 connected to the video processor 3 is touched, an electric current does not flow. Even when the endoscope 2 is connected to the adapter 5 after the adapter 5 is connected to the video processor 3, the connector receiver 5*b* is not in a state in which the power is supplied. Therefore, the power supply to the endoscope 2 including the image sensor 21 does not abruptly (in other words, without undergoing the sequence for starting power) start. Accordingly, the endoscope 2 including the image sensor 21 can be prevented from being damaged by an excessive electric current or the like.

When the first determination signal (model determination information) is received from the determination circuit 51*c*, the control circuit 51*a* determines that the endoscope 2 is connected to the adapter 5. At this time, the control circuit 51*a* further receives the second determination signal (sensor determination information) to determine the type of the image sensor 21.

When the connector 5*a* and the video processor 3 are connected and the connector receiver 5*b* and the endoscope 2 are connected (when the determination circuit 51*c* receives the first determination signal), the control circuit 51*a* causes the image sensor power circuit 54 to supply power to the endoscope 2.

The control circuit 51*a* produces an operation switching signal on the basis of the sensor determination information. The control circuit 51*a* transmits the operation switching signal to the image sensor power circuit 54, the image sensor drive circuit 53, and the video signal processing circuit 51*b*.

The image sensor power circuit 54 converts the power supplied from the power circuit 32 of the video processor 3 into the power (power for the image sensor) corresponding to the image sensor 21 of the single-use endoscope 2, in accordance with the operation switching signal and supplies the converted power to the endoscope 2. The power supplied from the power circuit 32 herein is the power corresponding to the reusable endoscope 2A. The image sensor power circuit 54 supplies the converted power to the image sensor 21 of the endoscope 2.

The image sensor drive circuit 53 switches the image sensor drive signal (including a synchronization signal and a drive signal) to a drive signal conforming to the image sensor 21, in accordance with the operation switching signal. The image sensor drive circuit 53 outputs the image sensor drive signal to the image sensor 21 to drive the image sensor 21. In this manner, a video signal is outputted from the image sensor 21.

The video reception circuit 55 receives the video signal from the image sensor 21 when the image sensor 21 is driven. The video reception circuit 55 transmits the received video signal to the video signal processing circuit 51*b*.

The video signal processing circuit 51*b* switches signal format conversion processing in accordance with the operation switching signal (in other words, in accordance with the type of the image sensor 21 determined based on the second determination signal). Then, the video signal processing circuit 51*b* receives the video signal, converts the received video signal into a video signal in a signal format processable by the video processor 3, and outputs the converted video signal to the video processor 3.

The ROM 52 stores, for example, conversion processing programs for a plurality of signal formats corresponding to combinations of a plurality of types of image sensors 21 of a plurality of models of single-use endoscopes 2 and a plurality of models of reusable endoscopes 2A that are connectable to the video processor 3. The video signal processing circuit 51*b* switches processing by selecting the signal format conversion processing program in accordance with the operation switching signal.

The video signal processing circuit 51*b* converts the format of the video signal by performing the set conversion processing. The converted format herein is the same as the format of the video signal outputted from the reusable endoscope 2A. The video signal processing circuit 51*b* transmits, to an image processing circuit 31 of the video processor 3, the video signal with the format converted. The image processing circuit 31 performs, on the received video signal, the same processing as the image processing performed on the video signal received from the reusable endoscope 2A. The video signal processing circuit 51*b* is directly or indirectly coupled via the second connector 5*b* to the insertion instrument to receive the second determination signal from the insertion instrument. The video signal processing circuit 51*b* is configured to receive a first video signal from the image sensor 21 included in the insertion instrument and to convert the first video signal into a second video signal in accordance with the type of the image sensor 21. The video signal processing circuit 51*b* is directly or indirectly coupled to the processor 3 to output the second video signal to the processor 3. The second determination signal is related to the type of the image sensor 21.

As described above, even when the adapter 5 is connected to the video processor 3 and the adapter 5 receives power supply from the video processor 3, in a case where the endoscope 2 is not connected to the adapter 5, the control circuit 51*a* causes the image sensor power circuit 54 to shut off supplying power to the endoscope 2 via the connector receiver 5*b*. Accordingly, even if the connector receiver 5*b* is externally exposed, the power is not supplied to the connector receiver 5*b*.

Figures 6, 7:
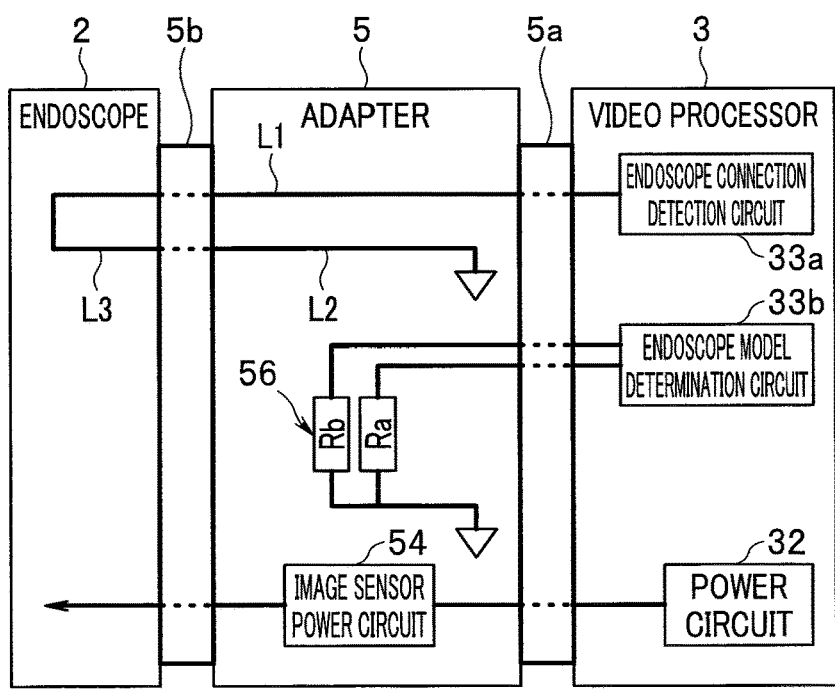
FIG. 6 is a table showing whether connection detection and power input are made in accordance with the connection state among the endoscope, the adapter, and the video processor in the aforementioned first embodiment.
FIG. 7 is a diagram showing a configuration example of a connection detection circuit for the single-use endoscope and the adapter for allowing the video processor to detect whether the reusable endoscope is connected, in the aforementioned first embodiment.

FIG. 6 is a table showing whether connection detection and power input are made in accordance with the connection state among the endoscope 2, the adapter 5, and the video processor 3 in the first embodiment.

As shown in column A of FIG. 6, when the video processor 3 and the adapter 5 are connected and the adapter 5 and the endoscope 2 are connected, the adapter 5 detects that the single-use endoscope 2 is connected. The video processor 3 detects that the reusable endoscope 2A is connected, with the configuration shown in FIG. 7, which will be described later. In this case, the video processor 3 supplies power (power input) from the power circuit 32 to execute the sequence for starting power of the endoscope.

As shown in column B of FIG. 6, when the video processor 3 and the adapter 5 are connected, but the adapter 5 and the endoscope 2 are not connected, the adapter 5 does not detect that the single-use endoscope 2 is connected. The video processor 3 detects that the reusable endoscope 2A is not connected, with the configuration shown in FIG. 8, which will be described later. In this case, the video processor 3 does not supply power (power input) from the power circuit 32 and does not execute the sequence for starting power of the endoscope.

Note that even when the adapter 5 and the endoscope 2 are connected, in a case where the video processor 3 and the adapter 5 are not connected, power is not supplied from the video processor 3 to the adapter 5 (and the endoscope 2). Thus, the adapter 5 cannot detect whether the endoscope 2 is connected. The video processor 3 also naturally detects that the reusable endoscope 2A is not connected.

FIG. 7 is a diagram showing a configuration example of a connection detection circuit for the single-use endoscope 2 and the adapter 5 for allowing the video processor 3 to detect whether the reusable endoscope 2A is connected, in the first embodiment.

Figure 8:
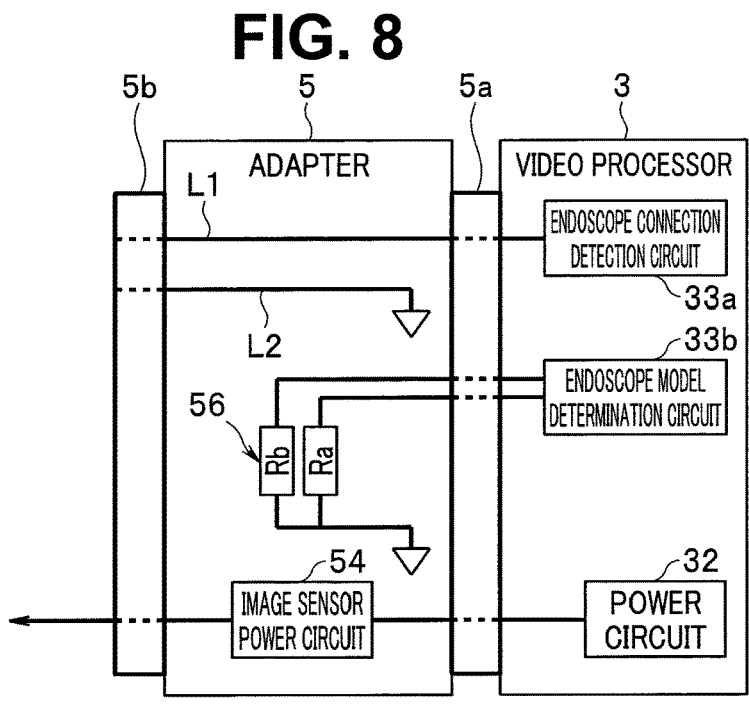
FIG. 8 is a diagram showing a configuration example of the connection detection circuit for the video processor and the adapter when the single-use endoscope is not connected, in the aforementioned first embodiment.

FIG. 8 is a diagram showing a configuration example of the connection detection circuit for the video processor 3 and the adapter 5 when the single-use endoscope 2 is not connected, in the first embodiment.

The video processor 3 includes an endoscope connection detection circuit 33*a* (connection detection circuit) and an endoscope model determination circuit 33*b* (insertion instrument determination circuit), in addition to the components shown in FIG. 5.

The adapter 5 includes first wiring L1 and second wiring L2. One end of the first wiring L1 is connected to the endoscope connection detection circuit 33*a* included in the video processor 3, via the connector 5*a* (first connector). The other end of the first wiring L1 is connected to one end of third wiring L3 included in the endoscope 2, via the connector receiver 5*b* (second connector).

One end of the second wiring L2 is grounded. The other end of the second wiring L2 is connected to the other end of the third wiring L3 that loops inside the endoscope 2, via the connector receiver 5*b* (second connector).

As shown in FIG. 7, when the endoscope 2, the adapter 5, and the video processor 3 are connected, the endoscope connection detection circuit 33*a* is grounded via the first wiring L1, the third wiring L3, and the second wiring L2. The first wiring L1 includes a first end and a second end, and the second wiring L2 includes a third end and a fourth end. The first end of the first wiring L1 is connected to the first connector 5*a*, the second end of the first wiring L1 is connected to the second connector 5*b*, the third end of the second wiring L2 is grounded, and the fourth end of the second wiring L2 is connected to the second connector 5*b*. A wire like cable and a circuit on a board can be used as the wirings. The insertion instrument comprises the third wiring L3 that loops inside the insertion instrument and includes a fifth end and a sixth end. The first end of the first wiring L1 is connected via the first connector 5*a* to a connection detection circuit included in the processor 3, the second end of the first wiring L1 is connected via the second connector 5*b* to the fifth end of the third wiring, the third end of the second wiring L2 is grounded, the fourth end of the second wiring L2 is connected via the second connector 5*b* to the sixth end of the third wiring. When the first connector 5*a* is connected to the processor 3 and the second connector 5*b* is connected to the insertion instrument, the switching circuit 51*a* permits the power circuit 54 to deliver the second power to the second connector 5*b*.

The endoscope connection detection circuit 33*a* monitors the voltage level of a connection detection signal. When it is detected that the voltage level of the connection detection signal is a ground voltage level, the endoscope connection detection circuit 33*a* detects that the endoscope is connected.

Then, the endoscope connection detection circuit 33*a* causes the endoscope model determination circuit 33*b* to determine the model of the endoscope as will be described below. Further, the endoscope connection detection circuit 33*a* causes the power circuit 32 to execute the sequence for starting power in accordance with the model of the endoscope. In this manner, when the endoscope connection detection circuit 33*a* detects the grounding, the video processor 3 supplies power to the adapter 5.

Meanwhile, as shown in FIG. 8, when the adapter 5 and the video processor 3 are connected, but the endoscope 2 is not connected, the voltage level of the connection detection signal is an open circuit voltage level that is different from the ground voltage level. Therefore, the endoscope connection detection circuit 33*a* does not detect grounding and detects that the endoscope is not connected. Thus, the endoscope connection detection circuit 33*a* does not cause the power circuit 32 to execute the sequence for starting power. Accordingly, the video processor 3 does not supply power to the adapter 5.

Next, the endoscope model determination circuit 33*b* determines the model of the endoscope as follows.

The adapter 5 further includes a first resistor unit 56. For example, in the configuration of FIG. 7, the first resistor unit 56 includes resistors Ra and Rb that are connected in parallel.

The first resistor unit 56 has a resistance value that is the same as the value of another resistor unit included in the reusable endoscope 2A (another insertion instrument) as one model of the plurality of models of reusable endoscopes 2A connectable to the video processor 3.

The first resistor unit 56 is connected to the endoscope model determination circuit 33*b* included in the video processor 3 via the connector 5*a* (first connector). In the example of FIG. 7, the resistors Ra and Rb connected in parallel are each connected to the endoscope model determination circuit 33b.

When the endoscope model determination circuit 33b detects the first resistor unit 56, the model of the endoscope that is connected to the video processor 3 is determined on the basis of the voltage value generated by the resistance value of the first resistor unit 56 or the like. In the example of FIG. 7, the endoscope model determination circuit 33b determines the model of the endoscope on the basis of the voltage value generated by the resistance value of the resistor Ra or the like and the voltage value generated by the resistance value of the resistor Rb or the like. The first resistor unit 56 has the first resistance value. The first resistor unit 56 is directly or indirectly coupled via the first connector 5a to an insertion instrument determination circuit 33b included in the processor 3 and the first resistor unit 56 is configured to generate the voltage value corresponding to the type of the image sensor 21. The second power corresponds to the voltage value. The first resistor unit 56 is provided around the FPGA 51.

As described above, the resistance value of the first resistor unit 56 is the same as the resistance value of another resistor unit included in the reusable endoscope 2A. Therefore, the endoscope model determination circuit 33b recognizes that the reusable endoscope 2A in the model determined from the voltage value generated by the resistance value or the like is connected, although the endoscope 2 and the adapter 5 in combination are actually connected.

In this manner, the adapter 5 includes the first resistor unit 56 having the same resistance value as the resistance value of another resistor unit included in the reusable endoscope 2A, which emulates that the reusable endoscope 2A is connected to the video processor 3.

Note that the signal that emulates that the reusable endoscope 2A is connected is not limited to the signal produced using the first resistor unit 56. For example, the signal for emulation may be transmitted from the ROM 52, or may be transmitted from the adapter 5 to the video processor 3 using any other techniques.

The power circuit 32 of the video processor 3 supplies power corresponding to the reusable endoscope 2A in the model that is determined by the endoscope model determination circuit 33b.

The image sensor power circuit 54 converts the power supplied from the video processor 3 to the reusable endoscope 2A into the power corresponding to the type of the image sensor 21 (the type determined based on the second determination signal) of the single-use endoscope 2. The image sensor power circuit 54 supplies the converted power to the endoscope 2.

According to such a first embodiment, a circuit to convert the format of a video signal is provided in the adapter 5 disposed between the endoscope 2 and the video processor 3. Thus, it is not required to provide a circuit to convert the format of the video signal in the endoscope 2. Accordingly, the production cost of the single-use endoscope 2 can be reduced. Since the adapter 5 is reusable, the operation cost can also be reduced.

The ROM 52 stores, for example, conversion processing programs for a plurality of signal formats corresponding to combinations of the plurality of models of single-use endoscopes 2 and the plurality of models of reusable endoscopes 2A. Thus, with the use of only one type of adapter 5, the plurality of models of single-use endoscopes 2 are also connectable to the video processor 3 that is compatible with any of the plurality of models of reusable endoscopes 2A.

The resistance value of the first resistor unit 56 included in the adapter 5 is the same as the resistance value of another resistor unit included in the reusable endoscope 2A. Thus, the video processor 3 determines that the model of the endoscope connected is the reusable endoscope 2A in a known model. Therefore, the video processor 3 only may execute the normal operation sequence (sequence of various operations including the sequence for starting power) performed when the reusable endoscope 2A is connected. Accordingly, the existing video processor 3 for the reusable endoscope 2A is applicable to the combination of the adapter 5 and the endoscope 2, without requiring to add any changes to the configuration.

The adapter 5 converts the power supplied for the reusable endoscope 2A from the video processor 3 into the power for the single-use endoscope 2 to be supplied. Thus, even when the endoscope 2 is in a type of performing power consumption different from the reusable endoscope 2A, the endoscope 2 can perform the normal operation.

The endoscope model determination circuit 33b of the video processor 3 is connected to the adapter 5 via the connector 5a, but is not connected to the endoscope 2. Therefore, the number of signal lines as an interface between the endoscope 2 and the adapter 5 can be reduced, so as to be able to simplify the configurations of the connector 2cl of the endoscope 2 and the connector receiver 5b of the adapter 5. As a result, the cost of the single-use endoscope 2 can be reduced.

When the endoscope 2 is not connected to the adapter 5, the control circuit 51a functions as a switching circuit to cause the image sensor power circuit 54 to shut off supplying power to the endoscope 2. Accordingly, the power supply to the image sensor 21 of the endoscope 2 via the connector receiver 5b is not performed.

Therefore, even when the endoscope 2 is connected to the adapter 5 after the adapter 5 is connected to the video processor 3, an excessive electric current is not supplied to the endoscope 2 or the like, to thus prevent the breakage of the endoscope 2 including the image sensor 21. When the endoscope 2 is not connected, even if the connector receiver 5b of the adapter 5 connected to the video processor 3 is touched, an electric current does not flow.

The configuration is made such that the endoscope connection detection circuit 33a of the video processor 3 is grounded via the first wiring L1 of the adapter 5, the third wiring L3 that loops inside the endoscope 2, and the second wiring L2 of the adapter 5. Therefore, when the adapter 5 and the video processor 3 are connected, but the adapter 5 and the endoscope 2 are not connected, the endoscope connection detection circuit 33a detects that the endoscope is not connected. Thus, the video processor 3 does not execute the sequence for starting power and does not supply power to the adapter 5.

Herein, if the configuration is made such that when only the adapter 5 is connected to the video processor 3, power is supplied, since the endoscope 2 is actually not connected, a response to the power supply cannot be obtained. Thus, the video processor 3 may possibly attempt to supply an excessive electric current or determine the sequence for starting power to be abnormal.

By contrast, according to the present embodiment, when the connection of the endoscope is not detected, the video processor 3 does not execute the sequence for starting power of the endoscope and does not supply power to the endoscope. In this manner, a situation can be avoided in which the video processor 3 determines that the sequence for starting power is abnormal.

Second Embodiment

Figure 9:
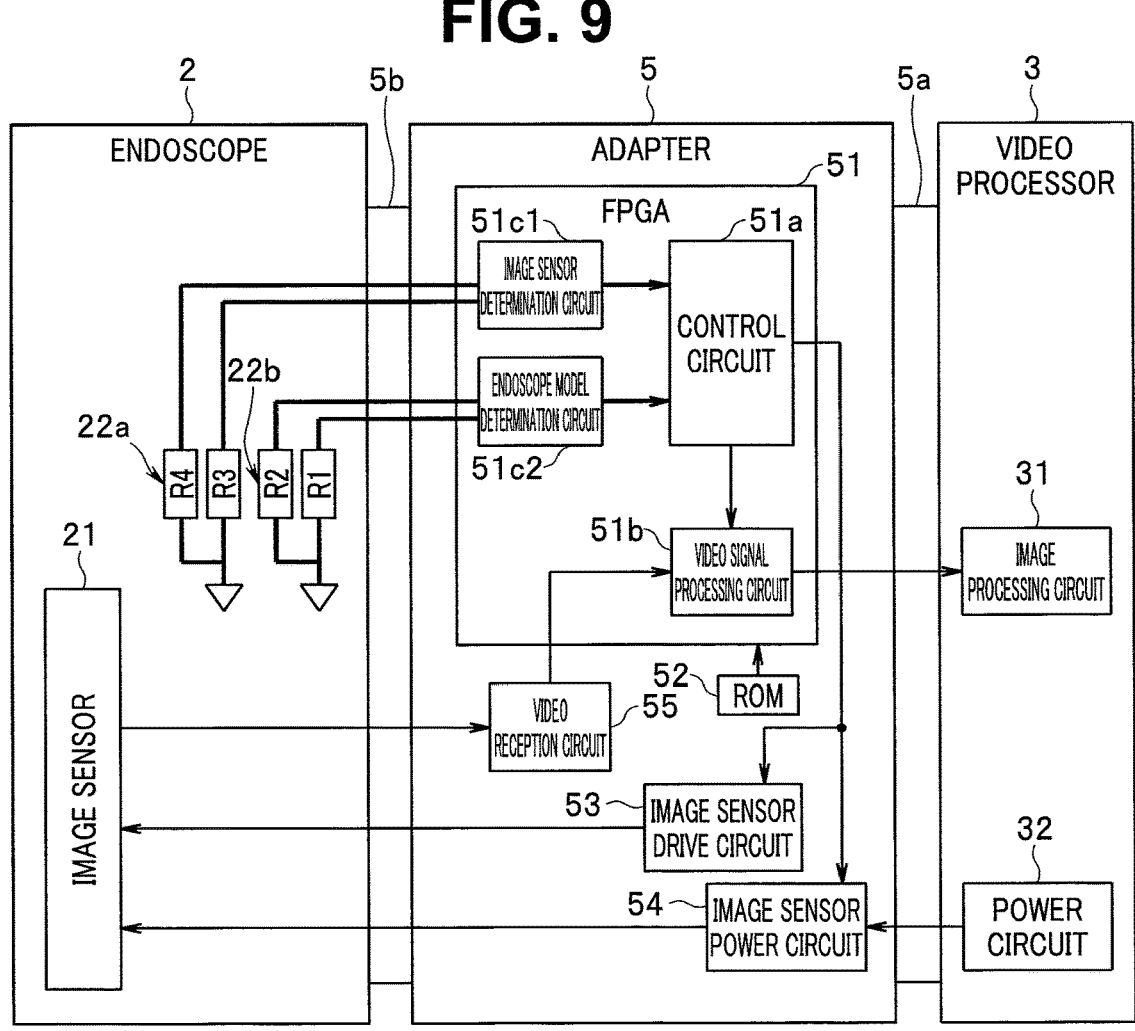
FIG. 9 is a block diagram showing the outline of electric configurations of the endoscope, the adapter, and the video processor in a second embodiment of the present disclosure.

FIG. 9 is a block diagram showing the outline of electric configurations of the endoscope 2, the adapter 5, and the video processor 3 in a second embodiment of the present disclosure. In the second embodiment, the same portions as the portions of the first embodiment are assigned the same reference numerals and the descriptions will be omitted, as appropriate. In the second embodiment, the points different from the first embodiment will mainly be described.

In the first embodiment, the determination information stored in the ROM 22 is retrieved, and the determination circuit 51*c* determines the model of the endoscope 2, the type of the image sensor 21, and the like. By contrast, in the present embodiment, in place of the ROM 22, the resistor units are provided in the single-use endoscope 2, so that the determination information is obtained on the basis of the resistance value. The first determination signal and the second determination signal are generated from the memory 22 included in the insertion instrument.

The FPGA 51 of the adapter 5 includes an image sensor determination circuit 51*cl* and an endoscope model determination circuit 51*c2* as the specific constituent elements of the determination circuit 51*c* (determination signal receiving circuit).

The single-use endoscope 2 includes a second resistor unit 22*b* having a second resistance value and a third resistor unit 22*a* having a third resistance value. The third resistor unit 22*a* is grounded at one end and is connected to the image sensor determination circuit 51*cl* at the other end via an image sensor detection line. The second resistor unit 22*b* is grounded at one end and is connected to the endoscope model determination circuit 51*c2* at the other end via a model detection line. The image sensor detection line and the model detection line are connected to the endoscope 2 and the adapter 5 via the connector receiver 5*b*.

For example, in the configuration of FIG. 9, the second resistor unit 22*b* includes resistors R1 and R2 connected in parallel. The resisters R1 and R2 connected in parallel are each connected to the endoscope model determination circuit 51*c2*. The third resistor unit 22*a* includes resistors R3 and R4 connected in parallel. The resistors R3 and R4 connected in parallel are each connected to the image sensor determination circuit 51*cl*.

The ROM 52 (memory) of the adapter 5 is a memory that retains first information indicating the relation between the second resistance value and the model of the endoscope 2. The ROM 52 further retains second information indicating the relation between the third resistance value and the type of the image sensor 21. The first information and the second information are retained in the ROM 52 as individual tables, for example.

The endoscope model determination circuit 51*c2* (determination signal receiving circuit) receives, for example, a voltage value generated from the second resistance value of the second resistor unit 22*b*, as the determination signal (model determination information). The endoscope model determination circuit 51*c2* determines the model of the endoscope 2 on the basis of the determination signal (model determination information) and the first information of the ROM 52. In this case, the first information includes information indicating the relation between the voltage value generated from the second resistance value or the like and the model of the endoscope 2. The determination signal receiving circuit 51*c2* is directly or indirectly coupled via the second connector 5*b* to the insertion instrument to receive the second determination signal from the insertion instrument. The determination signal receiving circuit 51*c* is configured to provide the first output corresponding to receiving the second determination signal and to provide a second output corresponding to not receiving the second determination signal. The determination signal receiving circuit 51*c2* is directly or indirectly coupled to the switching circuit 51*a* to deliver the first output and the second output to the switching circuit 51*a*. The switching circuit 51*a* is configured to operate the power circuit 54 to deliver the second power to the second connector 5*b* when the switching circuit 51*a* delivers the first output, and operate the power circuit 54 to prevent delivery of the second power to the second connector when the switching circuit 51*a* delivers the second output. The second determination signal is related to the model of the insertion instrument.

The image sensor determination circuit 51*cl* receives, for example, a voltage value generated from the third resistance value of the third resistor unit 22*a*, as the second determination signal. The image sensor determination circuit 51*cl* determines the type of the image sensor 21 on the basis of the second determination signal and the second information of the ROM 52. In this case, the second information includes information indicating the relation between the voltage value generated from the third resistance value or the like and the type of the image sensor 21.

According to such a second embodiment, substantially the same advantageous effects as the advantageous effects of the aforementioned first embodiment are produced.

According to the second embodiment, it provides the single-use endoscope 2 with the second resistor unit 22*b* and the third resistor unit 22*a* in place of the ROM 22. Therefore, the parts cost and the number of parts are reduced, to thus enable the production cost of the single-use endoscope 2 to be further reduced.

Third Embodiment

Figure 10:
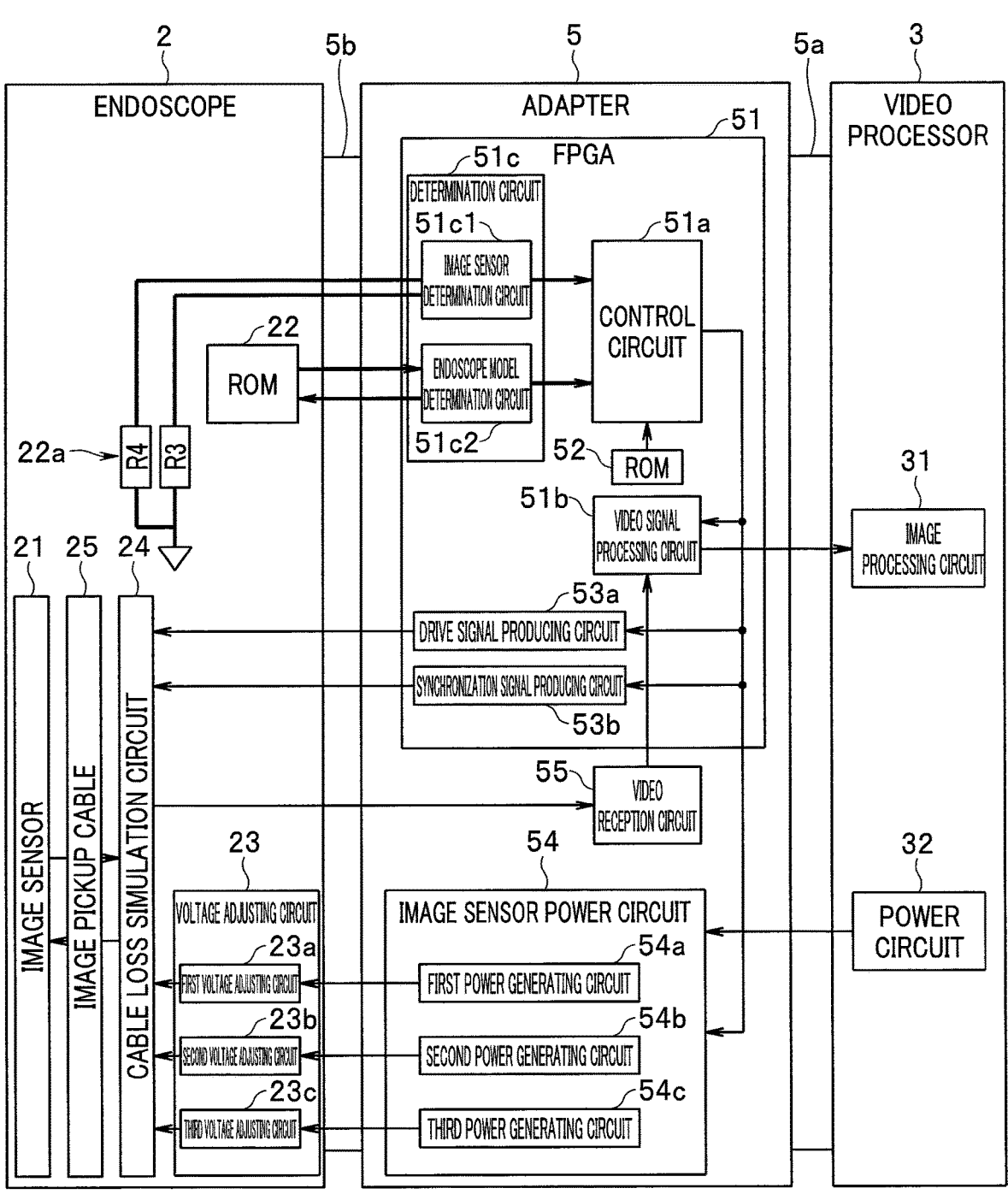
FIG. 10 is a block diagram showing the outline of electric configurations of the endoscope, the adapter, and the video processor in a third embodiment of the present disclosure.

FIG. 10 is a block diagram showing the outline of electric configurations of the endoscope 2, the adapter 5, and the video processor 3 in a third embodiment of the present disclosure. In the third embodiment, the same portions as the portions of the first and the second embodiments are assigned the same reference numerals and the descriptions will be omitted, as appropriate. In the third embodiment, the points different from the first and the second embodiments will mainly be described.

Similarly to the second embodiment, the determination circuit 51*c* (determination signal receiving circuit) includes the image sensor determination circuit 51*cl* and the endoscope model determination circuit 51*c2*.

The endoscope 2 includes the ROM 22 and the third resistor unit 22*a*. The ROM 22 is connected to the endoscope model determination circuit 51*c2* (determination signal receiving circuit). The ROM 22 includes, as the determination information, the model determination information (model information of the endoscope 2). The third resistor unit 22*a* is connected to the image sensor determination circuit 51*cl*. As described above, the third resistor unit 22*a* includes the third resistance value for determining the type of the image sensor 21. The determination signal receiving circuit 51*c2* is directly or indirectly coupled via the second connector 5*b* to the insertion instrument to receive the second determination signal from the insertion instrument. The determination signal receiving circuit 51*c* is configured to provide the first output corresponding to receiving the second determination signal and to provide a second output corresponding to not receiving the second determination signal. The determination signal receiving circuit 51*c*2 is directly or indirectly coupled to the switching circuit 51*a* to deliver the first output and the second output to the switching circuit 51*a*. The switching circuit 51*a* is configured to operate the power circuit 54 to deliver the second power to the second connector 5*b* when the switching circuit 51*a* delivers the first output, and operate the power circuit 54 to prevent delivery of the second power to the second connector when the switching circuit 51*a* delivers the second output. The second determination signal is related to the model of the insertion instrument.

In the adapter 5 of the first and the second embodiments, the ROM 52 is provided outside the FPGA 51, and in the adapter 5 of the present embodiment, the ROM 52 is provided inside the FPGA 51.

In the adapter 5 of the first and the second embodiments, the image sensor drive circuit 53 provided outside the FPGA 51 drives the image sensor 21. By contrast, in the adapter 5 of the present embodiment, a drive signal producing circuit 53*a* and a synchronization signal producing circuit 53*b* that correspond to the image sensor drive circuit 53 are provided inside the FPGA 51. The drive signal producing circuit 53*a* produces a drive signal and transmits the drive signal to the endoscope 2. The synchronization signal producing circuit 53*b* produces a synchronization signal and transmits the synchronization signal to the endoscope 2.

In other words, in the present embodiment, since the FPGA 51 is configured to drive the image sensor 21, a drive circuit may be provided separately from the FPGA 51, thereby enabling to further simplify the configuration of the adapter 5.

The image sensor power circuit 54 of the adapter 5 converts the power supplied from the power circuit 32 of the video processor 3 into the power corresponding to a standard endoscope (standard insertion instrument) including a cable having a first length and supplies the converted power. The standard endoscope herein is the endoscope 2 as one model of the plurality of models of single-use endoscopes 2 to which the adapter 5 is adaptable. The cable has a length sufficient to transmit the first power to the second power via the second connector 5*b*, and an adjustment circuit configured to adjust the second power based on the length of the cable.

The image sensor power circuit 54 includes a first power generating circuit 54*a*, a second power generating circuit 54*b*, and a third power generating circuit 54*c*. The first power generating circuit 54*a*, the second power generating circuit 54*b*, and the third power generating circuit 54*c* are each configured as, for example, a LDO (low drop out) regulator. With the use of the LDO regulator, the first power generating circuit 54*a*, the second power generating circuit 54*b*, and third power generating circuit 54*c* can obtain a output voltage even if the input/output voltage difference (dropout) is small.

The single-use endoscope 2 further includes a voltage adjusting circuit 23, a cable loss simulation circuit 24, and an image pickup cable 25.

The voltage adjusting circuit 23 includes a first voltage adjusting circuit 23*a* connected to the first power generating circuit 54*a*, a second voltage adjusting circuit 23*b* connected to the second power generating circuit 54*b*, and a third voltage adjusting circuit 23*c* connected to the third power generating circuit 54*c*.

The first voltage adjusting circuit 23*a* adjusts the voltage of the power from the first power generating circuit 54*a* and supplies the power to the image sensor 21 side.

The second voltage adjusting circuit 23*b* adjusts the voltage of the power from the second power generating circuit 54*b* and supplies the power to the image sensor 21 side.

The third voltage adjusting circuit 23*c* adjusts the voltage of the power from the third power generating circuit 54*c* and supplies the power to the image sensor 21 side.

The cable loss simulation circuit 24 is connected to the drive signal producing circuit 53*a*, the synchronization signal producing circuit 53*b*, the video reception circuit 55, and the voltage adjusting circuit 23. The cable loss simulation circuit 24 is further connected to the image sensor 21 via the image pickup cable 25.

The image pickup cable 25 transmits, to the image sensor 21, the power supplied via the connector receiver 5*b*, the power having the voltage adjusted by the voltage adjusting circuit 23. The image pickup cable 25 transmits the drive signal transmitted from the drive signal producing circuit 53*a* and the synchronization signal transmitted from the synchronization signal producing circuit 53*b* to the image sensor 21. The image pickup cable 25 further transmits the video signal transmitted from the image sensor 21 to the video reception circuit 55.

The image pickup cable 25 of the endoscope 2 has a second length. The second length of the image pickup cable 25 of the endoscope 2 generally differs from the first length of the cable of the standard endoscope. In other words, the length of the endoscope 2 differs depending on the models and the length of the image pickup cable 25 mounted differs.

Thus, the voltage adjusting circuit 23 adjusts a power difference resulting from the difference between the second length and the first length.

When the length of the image pickup cable 25 differs, the signal transmission loss of the image pickup cable 25 differs. When the signal transmission loss differs, there is a possibility that not all the models of endoscopes 2 can be driven by the circuit included in the adapter 5. Thus, the cable loss simulation circuit 24 is provided in the endoscope 2 so as to compensate the difference in the signal transmission loss due to the difference in the length of the image pickup cable 25. In this manner, the cable loss simulation circuit 24 compensates the transmission loss of the power, the drive signal, the synchronization signal, and the video signal.

According to such a third embodiment, substantially the same advantageous effects as the advantageous effects of the aforementioned first and second embodiments are produced.

According to the third embodiment, with one type of the adapter 5, the plurality of models of endoscopes 2 having the image pickup cables 25 significantly differing in length are connectable. Therefore, the versatility of the adapter 5 is improved.

Fourth Embodiment

Figure 11:
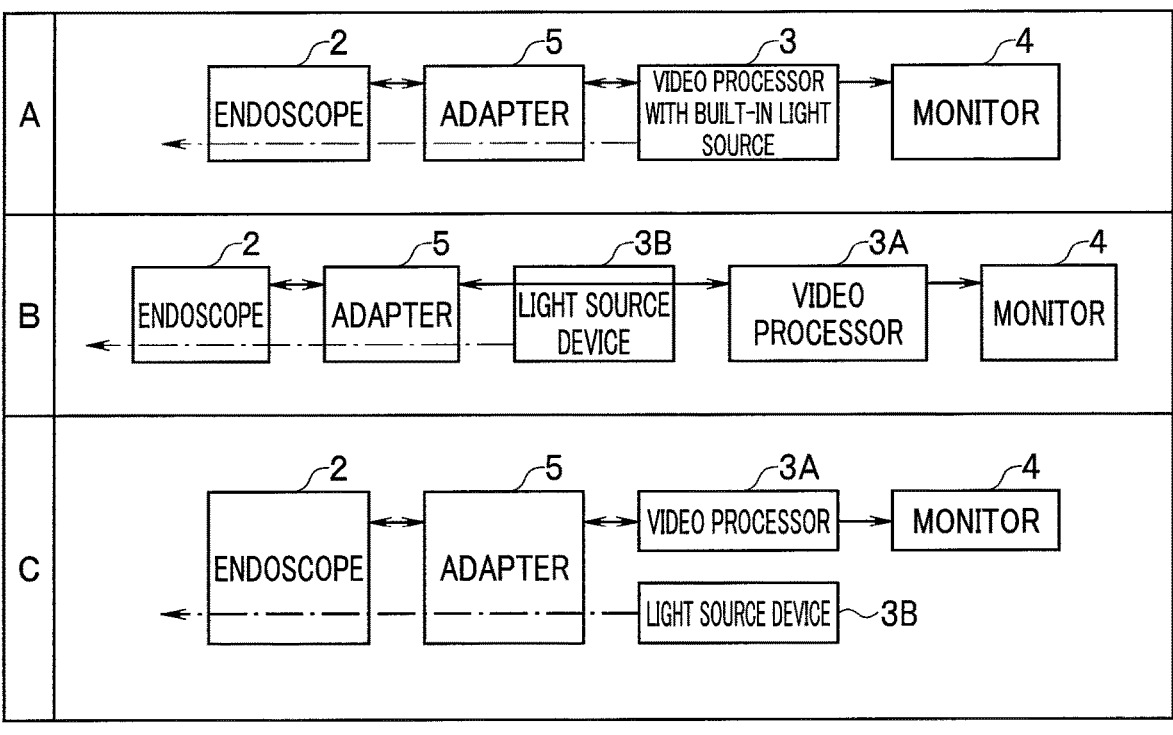
FIG. 11 is a table showing a configuration example of the endoscope system in a fourth embodiment of the present disclosure.

FIG. 11 is a table showing a configuration example of the endoscope system 1 in a fourth embodiment of the present disclosure. In the fourth embodiment, the same portions as the portions of the first to third embodiments are assigned the same reference numerals and the descriptions will be omitted, as appropriate. In the fourth embodiment, the points different from the first to third embodiments will mainly be described.

FIG. 11 shows some configuration examples of the endoscope system 1 configured with the single-use endoscope 2.

In columns A to C of FIG. 11, the solid arrows in the leftward direction indicate a clock, a synchronization signal, and a control communication. The solid arrows in the rightward direction indicate a video signal and the control communication. The solid arrows in the rightward direction entering the monitor 4 indicate an image signal. The dashed-dotted lines in the leftward direction indicate illumination light.

In the first configuration example shown in column A of FIG. 11, the video processor 3 is in a light source built-in type as described in the aforementioned embodiments. The single-use endoscope 2 is connected to the video processor 3 via the adapter 5. The adapter 5 transmits/receives an electric signal to/from the endoscope 2 and the video processor 3. The video processor 3 supplies illumination light to the endoscope 2 via the adapter 5. The adapter 5 receives a video signal from the endoscope 2 and processes the video signal by the video signal processing circuit 51*b*. The video processor 3 receives the video signal from the adapter 5. The video processor 3 processes the video signal received from the adapter 5 by the image processing circuit 31 and outputs an image signal to the monitor 4.

In the second configuration example shown in column B of FIG. 11, a light source device 3B and a video processor 3A are provided as separate bodies. The single-use endoscope 2 is connected to the light source device 3B and the video processor 3A in sequence (in series) via the adapter 5. The light source device 3B supplies illumination light to the endoscope 2 via the adapter 5. The light source device 3B relays an electric signal from the video processor 3 to the adapter 5 via an electric contact. The light source device 3B relays an electric signal from the adapter 5 to the video processor 3A via the electric contact. In this manner, the video processor 3A receives a video signal from the adapter 5 via the light source device 3B. The video processor 3A processes the video signal received from the adapter 5 by the image processing circuit 31 and outputs an image signal to the monitor 4.

In the third configuration example shown in column C of FIG. 11, the light source device 3B and the video processor 3A are provided as separate bodies. The adapter 5 is connected to both the light source device 3B and the video processor 3A. In other words, the light source device 3B and the video processor 3A are connected to the adapter 5 in parallel. The light source device 3B supplies illumination light to the endoscope 2 via the adapter 5. The adapter 5 transmits/receives an electric signal to/from the video processor 3A via the electric contact. For example, the adapter 5 receives power supply from the video processor 3A. The video processor 3A receives a video signal from the adapter 5. The video processor 3A processes the video signal received from the adapter 5 by the image processing circuit 31 and outputs an image signal to the monitor 4.

In any of the first to third configuration examples, the adapter 5 receives illumination light from the light source inside the video processor 3 or the light source device 3B and receives an electric signal from the video processor 3. The adapter 5 supplies illumination light to the endoscope 2 and drives the endoscope 2 with the electric signal. Further, the adapter 5 transmits a video signal from the endoscope 2 to the video processor 3, 3A. Thus, the adapter 5 includes both an optical path for transmitting the illumination light and a signal wire for transmitting the electric signal.

Note that the video processor 3 in a light source built-in type of the first configuration example constitutes the processor that performs processing related to the endoscope. The combinations of the light source device 3B and the video processor 3A of the second configuration example and the third configuration example also constitute the processor that performs processing related to the endoscope.

According to such a fourth embodiment, with any of the first to third configuration examples adopted, substantially the same advantageous effects as the advantageous effects of the aforementioned first to third embodiments are produced.

Fifth Embodiment

Figure 12:
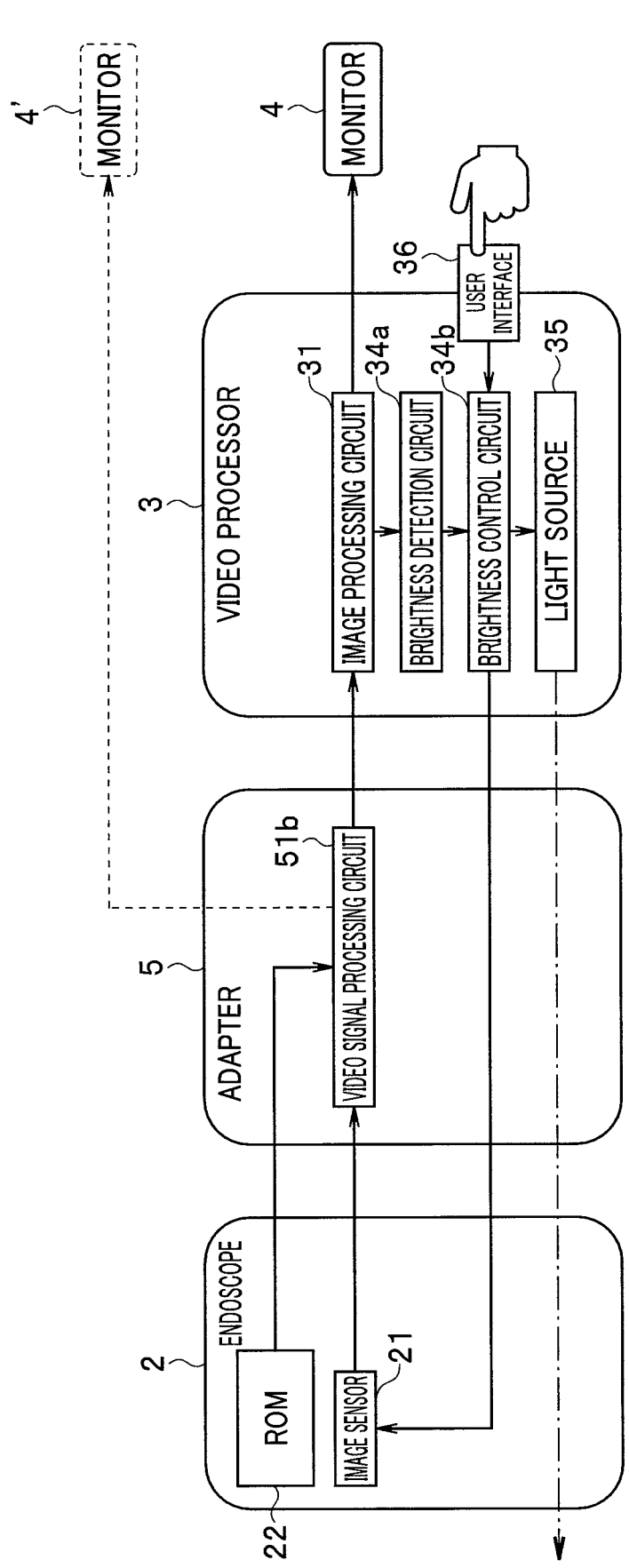
FIG. 12 is a diagram showing a configuration example of the endoscope system in a fifth embodiment of the present disclosure.

FIG. 12 is a diagram showing a configuration example of the endoscope system 1 in a fifth embodiment of the present disclosure. In the fifth embodiment, the same portions as the portions of the first to fourth embodiments are assigned the same reference numerals and the descriptions will be omitted, as appropriate. In the fifth embodiment, the points different from the first to fourth embodiments will mainly be described.

The video processor 3 is, for example, in a light source built-in type and includes a built-in light source 35. The video processor 3 further includes a brightness detection circuit 34*a*, a brightness control circuit 34*b*, and a user interface 36.

The image processing circuit 31 transmits, to the brightness detection circuit 34*a*, any one of a video signal received from the video signal processing circuit 51*b*, a signal obtained by partially performing image processing on the received video signal, and an image signal obtained by performing image processing on the video signal.

The brightness detection circuit 34*a* detects the brightness of a subject on the basis of the signal received from the image processing circuit 31 to produce brightness information. The brightness detection circuit 34*a* transmits the produced brightness information to the brightness control circuit 34*b*.

The brightness control circuit 34*b* is connected to the user interface 36. The user sets a target brightness of the subject using the user interface 36 of the video processor 3. The user interface 36 may also perform other settings on the endoscope system 1.

The target brightness set by the user interface 36 is inputted into the brightness control circuit 34*b*. The brightness control circuit 34*b* produces a light source control signal and an electronic shutter control signal that allow the subject to have the target brightness. The brightness control circuit 34*b* transmits the light source control signal to the light source 35 and the electronic shutter control signal to the image sensor 21.

The light source 35 adjusts the brightness of the illumination light on the basis of the light source control signal received from the brightness control circuit 34*b* and emits the adjusted illumination light. The emitted illumination light is transmitted to the endoscope 2 via the adapter 5.

The image sensor 21 sets an exposure time period on the basis of the electronic shutter control signal received from the brightness control circuit 34*b*. The image sensor 21 then performs photoelectric conversion, only for the exposure time period, on an optical image of the subject irradiated with the illumination light to produce a video signal. The image sensor 21 transmits the produced video signal to the video signal processing circuit 51*b*.

The video signal processing circuit 51*b* converts the format of the video signal on the basis of the determination information retrieved from the ROM 22 and transmits the converted signal to the image processing circuit 31.

Note that as described in FIG. 7, FIG. 8, and the like by showing the examples, the adapter 5 transmits, to the video processor 3, a signal emulating that the reusable endoscope 2A is connected. The adapter 5 may additionally transmit the determination information retrieved from the ROM 22 to the video processor 3.

The video signal processing circuit 51*b* also performs image processing to produce an image signal for display, other than the format conversion for transmission to the image processing circuit 31. The video signal processing circuit 51*b* is connectable to, for example, an external monitor 4', without using the video processor 3. The video signal processing circuit 51*b* transmits the produced image signal for display to the monitor 4'. In this manner, the monitor 4' displays an endoscope image. Note that the monitor 4' may be connected, and is thus denoted with a dotted line in FIG. 12.

The image processing circuit 31 outputs, to the monitor 4, the image signal on which the image processing is performed. The monitor 4 also displays the endoscope image accordingly.

Note that the brightness information detected by the brightness detection circuit 34*a* and the target brightness set by the user interface 36 may be fed back to the image processing circuit 31. In this case, the image processing circuit 31 may superimpose the brightness information and the target brightness over the endoscope image, as an indicator, for example. In this manner, the indicator is displayed together with the endoscope image on the monitor 4.

According to such a fifth embodiment, substantially the same advantageous effects as the advantageous effects of the aforementioned first to fourth embodiments are produced.

According to the fifth embodiment, since the adapter 5 includes the function of outputting an image signal displayable on the monitor 4', the options for outputting the image increase. For example, when power is supplied to the adapter 5 from a separate power device, observation of the endoscope image is available without the video processor 3.

According to the fifth embodiment, with the use of the user interface 36 provided in the video processor 3, the brightness of the illumination light, and eventually, the brightness of a subject can be adjusted to brightness.

Note that FIG. 12 shows the example of the video processor 3 provided with the user interface 36, but the embodiment is not limited to such an example. For example, the brightness control circuit 34*b* may adjust the brightness of the illumination light such that a touch panel as the user interface 36 is provided in the monitor 4 and the user operates the touch panel. Other image adjustments and other settings on the endoscope system 1 may be performed by operating the touch panel.

Sixth Embodiment

Figure 13:
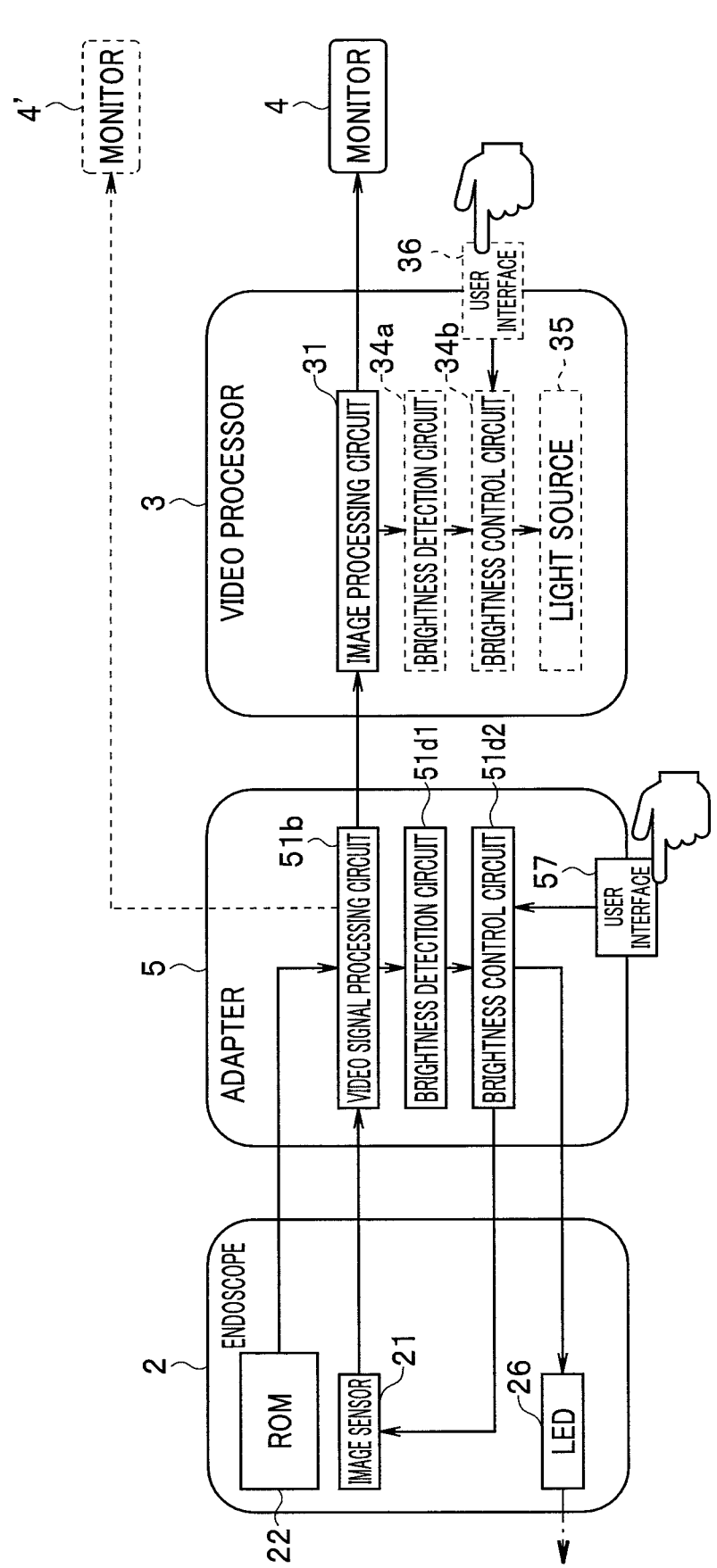
FIG. 13 is a diagram showing a configuration example of the endoscope system in a sixth embodiment of the present disclosure.

FIG. 13 is a diagram showing a configuration example of the endoscope system 1 in a sixth embodiment of the present disclosure. In the sixth embodiment, the same portions as the portions of the first to fifth embodiments are assigned the same reference numerals and the descriptions are omitted, as appropriate. In the sixth embodiment, the points different from the first to fifth embodiments will mainly be described.

The endoscope system 1 shown in FIG. 13 is the endoscope system 1 shown in FIG. 12 with the following components added.

The endoscope 2 includes an LED 26 as a light source in the distal end portion 2*al* of the insertion portion 2*a*.

The adapter 5 includes a brightness detection circuit 51*d*1, a brightness control circuit 51*d*2, and a user interface 57.

The video signal processing circuit 51*b* transmits, to the brightness detection circuit 51*d*1, any one of a video signal received from the image sensor 21, a video signal obtained by converting the format of the received video signal, and an image signal for display that is produced from the video signal.

The brightness detection circuit 51*d*1 detects the brightness of a subject on the basis of the signal received from the video signal processing circuit 51*b* to produce brightness information. The brightness detection circuit 51*d*1 transmits the produced brightness information to the brightness control circuit 51*d*2.

The brightness control circuit 51*d*2 is connected to the user interface 57. The user sets a target brightness of the subject using the user interface 57 of the adapter 5. The user interface 57 may also perform other settings on the endoscope system 1.

The target brightness set by the user interface 57 is inputted into the brightness control circuit 51*d*2. The brightness control circuit 51*d*2 adjusts a drive electric current of the LED 26, using pulse width modulation, for example, so that the subject has the target brightness. The brightness control circuit 51*d*2 produces an electronic shutter control signal that allows the subject to have the target brightness. The brightness control circuit 51*d*2 outputs the adjusted drive electric current to the LED 26 and transmits the electronic shutter control signal to the image sensor 21.

The LED 26 receives the drive electric current to emit illumination light. The emitted illumination light is emitted from the distal end portion 2*al* toward the subject.

The image sensor 21 sets an exposure time period on the basis of the electronic shutter control signal received from the brightness control circuit 51*d*2. The image sensor 21 then performs photoelectric conversion, only for the exposure time period, on an optical image of the subject irradiated with the illumination light to produce a video signal. The image sensor 21 transmits the produced video signal to the video signal processing circuit 51*b*.

In the present embodiment, the illumination light is adjusted by the endoscope 2 and the adapter 5. Therefore, the brightness detection circuit 34*a*, the brightness control circuit 34*b*, the light source 35, and the user interface 36 of the video processor 3 are not used for adjustment of the illumination light, and thus, are denoted with dotted lines in FIG. 13. However, it goes without saying that the user interface 36 and the like may also be used for purposes other than the adjustment of the illumination light.

In a case of the configuration in which the video processor 3 detects the light source connector on the endoscope side to start supplying illumination light, it is recommended that the length of the light source connector of the connector 5*a* of the adapter 5 should be differentiated from the normal length (for example, the length is made shorter than normal so as to disable the video processor 3 to detect the light source connector) so as to avoid emission of the illumination light from the video processor 3.

Alternatively, the adapter 5 may be provided with a mechanism to dim the illumination light incident from the video processor 3. It is recommended that the dimming mechanism should prevent heat generation due to the illumination light inside the adapter 5 and light leakage from the inside of the adapter 5.

Note that the brightness information detected by the brightness detection circuit 51*dl* and the target brightness set by the user interface 57 may be fed back to the video signal processing circuit 51*b*. In this case, the video signal processing circuit 51*b* may superimpose the brightness information and the target brightness over the endoscope image, as an indicator. In this manner, the indicator is displayed together with the endoscope image on the monitor 4'. The video signal processing circuit 51b may transmit the video signal over which the indicator is superimposed to the image processing circuit 31 to display the indicator on the monitor 4 as well.

FIG. 13 shows the configuration example in which the LED 26 is provided in the distal end portion 2al of the endoscope 2, but the LED 26 may be provided, not only in the distal end portion 2a1, but in the operation portion 2b, the connector 2cl, or the like, so as to perform transmission through the light guide to the distal end portion 2al. The configuration may be made such that the light source such as the LED 26 is provided in the adapter 5 so as to supply the illumination light from the adapter 5 to the endoscope 2.

The user interface 57 may be provided not only in the adapter 5, but also in the endoscope 2.

According to such a sixth embodiment, substantially the same advantageous effects as the advantageous effects of the aforementioned first to fifth embodiments are produced.

According to the sixth embodiment, also in a case where the single-use endoscope 2 or the adapter 5 includes the light source, such as the LED 26, the brightness of the illumination light can be adjusted.

Seventh Embodiment

Figure 14:
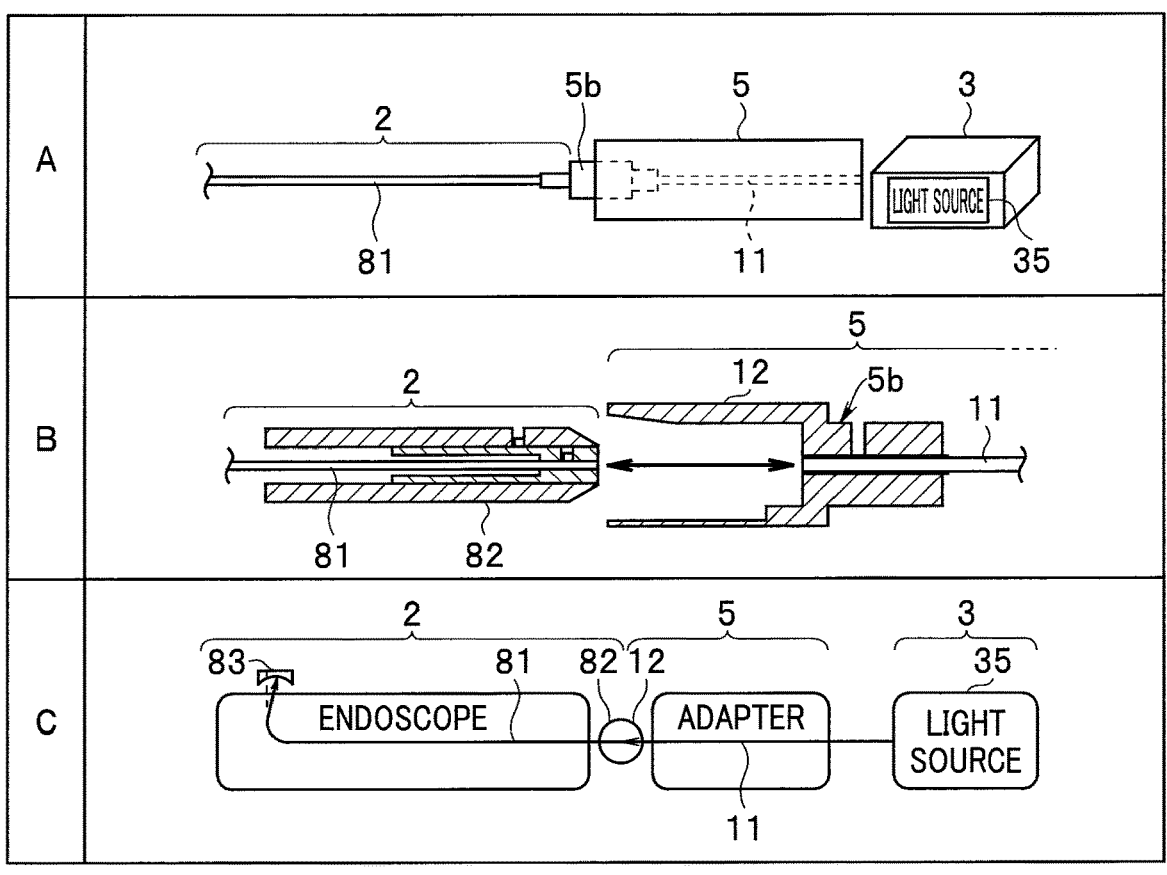
FIG. 14 is a table showing configurations of light guides inside the endoscope and the adapter of the endoscope system in a seventh embodiment of the present disclosure.

FIG. 14 to FIG. 18 show a seventh embodiment of the present disclosure. FIG. 14 is a table showing configurations of light guides inside the endoscope 2 and the adapter 5 of the endoscope system 1 in the seventh embodiment. In the seventh embodiment, the same portions as the portions of the first to sixth embodiments are assigned the same reference numerals and the descriptions are omitted, as appropriate. In the seventh embodiment, the points different from the first to sixth embodiments will mainly be described.

As shown in column A of FIG. 14, the adapter 5 includes a glass light guide (glass LG) 11 as a light guide that relays illumination light emitted from the light source 35 of the video processor 3 to the endoscope 2.

The glass LG11 takes in the illumination light supplied from the light source 35 included in the video processor 3 via the connector 5a, and guides and emits the illumination light to the endoscope 2, via the connector receiver 5b. The use of the glass LG 11 can improve the heat resistance.

Further, since the glass LG 11 is used in the adapter 5 disposed midway between the video processor 3 and the endoscope 2, a plastic light guide (PLG) 81 disposed on the endoscope 2 side, as will be described later, can be prevented from being melted, burnt, discolored, and deformed due to the heat of the illumination light transmitted from the light source 35 with a high power.

Figure 17:
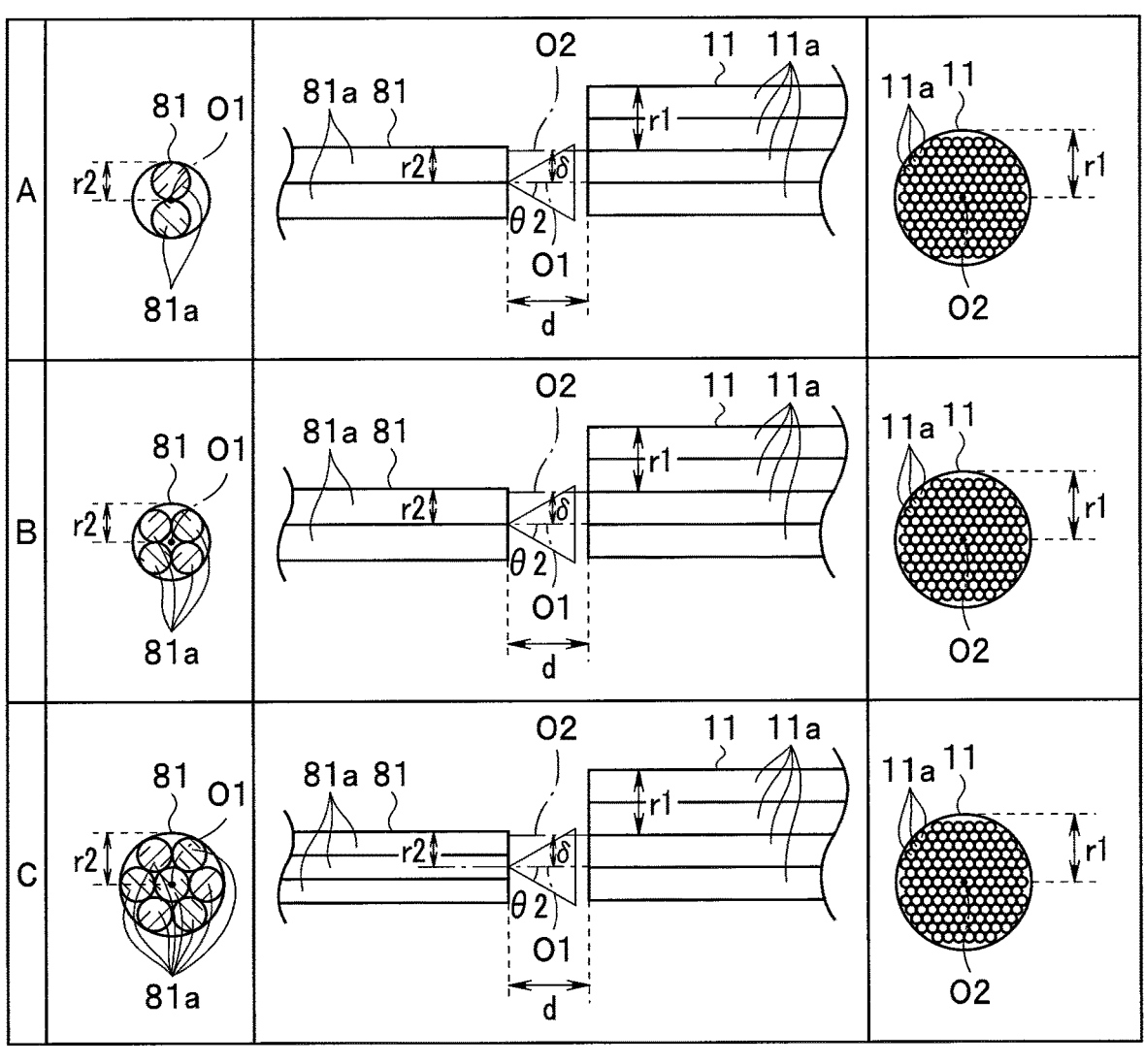
FIG. 17 is a table for description of some examples of the glass LG and the PLG in the aforementioned seventh embodiment.

The glass LG 11 includes a glass fiber bundle in which a plurality of strands 11a of glass fibers are bundled, as shown in FIG. 17 or the like, which will be described later. The glass LG 11 is formed as a glass fiber bundle instead of a glass rod, so that the flexibility in the member arrangement inside the adapter 5 increases. Thus, enlargement of the adapter 5 in size can be suppressed.

The endoscope 2 includes the plastic light guide (PLG) 81. The PLG 81 is a second light guide that guides the illumination light taken in through the glass LG 11 of the adapter 5 to, for example, the distal end of the endoscope 2.

Figure 15:
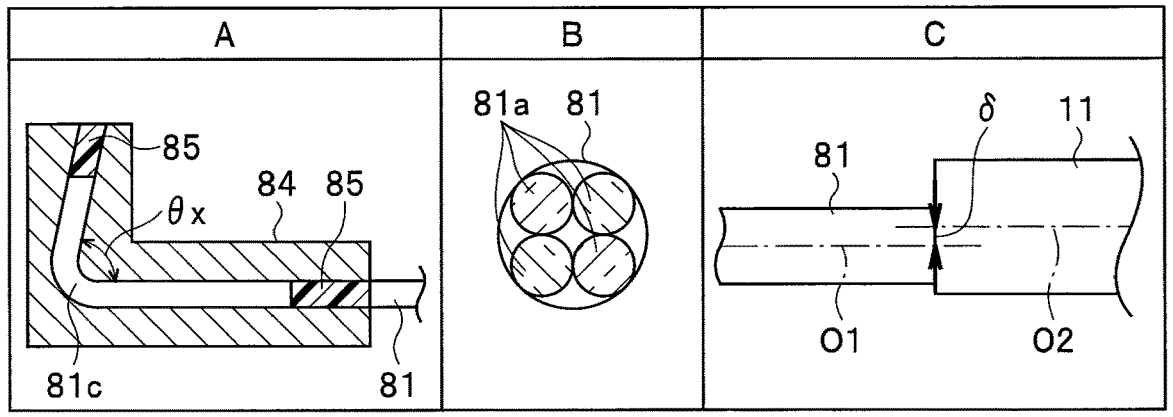
FIG. 15 is a table showing configurations of a glass LG and a PLG in the aforementioned seventh embodiment.

FIG. 15 is a table showing configurations of the glass LG 11 and the PLG 81 in the seventh embodiment.

As shown in column B of FIG. 15, the PLG 81 includes a resin fiber bundle in which a plurality of strands 81a (for example, 20 strands or fewer) of transparent resin fibers are bundled. The strand 81a is a plastic light guide having a diameter of several hundred μm, for example. Thus, the flexibility is excellent as compared to a case in which a glass LG is used, and the flexibility in the arrangement inside the endoscope 2 is high. As compared to a case in which the PLG 81 is configured with one single strand having a diameter lager than the diameter of the strand 81a, the flexibility is excellent so that the reduction of the light amount in a bending portion can be suppressed.

Forming the PLG 81 with twenty or fewer strands 81a does not require application of an antifriction agent in a case of forming a fiber bundle with several hundreds to several thousands of fibers bundled, thereby enabling to reduce the production cost.

Further, since the PLG is reasonable in price as compared to the glass LG, the production cost of the endoscope 2 can be reduced. Thus, the configuration is suitable for the single-use endoscope 2 for which cost reduction is desired.

The strands 81a are formed with plastic material having a melting point of 85° C. or higher, for example. Thus, the strand 81a can be prevented from being melted, burnt, discolored, and deformed by the illumination light.

As shown in column B of FIG. 14, a light guide connector 82 provided in the connector 2cl of the endoscope 2 is detachable from a light guide receiver 12 provided in the connector receiver 5b of the adapter 5. Thus, the plurality of models of endoscopes 2 are connectable to the same adapter 5.

As shown in column C of FIG. 15, when the glass LG 11 and the PLG 81 abut against each other, a disparity in an eccentricity δ (optical axis deviation) occasionally occurs between the optical axis (center axis) 01 of the PLG 81 and the optical axis (center axis) 02 of the glass LG 11. Thus, the transmission efficiency of the illumination light is occasionally degraded due to the disparity in the eccentricity δ. A configuration to suppress such degradation in the transmission efficiency of the illumination light will be described later with reference to FIG. 16 to FIG. 18. The light guide has a first end and a second end. The light guide is configured to receive at the first end an illumination light from a light source received via the first connector 5a and guide the received illumination light to the second end, and deliver guided illumination light to the insertion instrument via the second connector 5b.

As shown in column C of FIG. 14, the PLG 81 is bent, for example, in the side face direction in the distal end portion 2al of the endoscope 2, and emits illumination light toward a subject from an illumination lens 83 provided on the side face of the distal end portion 2al. The illumination lens 83 is configured with one concave lens, for example. Configuring the illumination lens 83 with one concave lens can reduce cost and weight.

A bending angle θx of the PLG 81 shown in column A of FIG. 15 is less than 90°. In other words, the PLG 81 is bent at an angle greater than 90° in a bending portion 81c (that is, directed slightly rearward than sideward).

The PLG 81 is bent at an angle greater than 90° and the concave lens is used as the illumination lens 83, so that a wide area including the rear side than the lateral side can be irradiated with the illumination light, thereby increasing the illumination light reaching the area of field of view of image pickup without lacking the light amount in the surroundings.

As shown in column A of FIG. 15, a distal end portion including the bending portion 81c of the PLG 81 is fixed to a frame 84 inside the distal end portion 2al using an adhesive 85. At this time, the adhesive 85 is applied onto a linear portion of the PLG 81, but not onto the bending portion 81c. Adoption of such a configuration can suppress leakage of the illumination light in the bending portion 81c, to thus suppress the reduction in the amount of light emitted from the illumination lens 83.

As compared to the case in which the light source is disposed inside the endoscope 2, the light source 35 disposed inside the video processor 3 is less restrictive in size, power, or the like. Therefore, the light source 35 may include a special light source or the like, in addition to a white light source. Thus, with the adoption of the configuration in which the illumination light emitted from the light source 35 disposed inside the video processor 3 is transmitted by means of the glass LG 11 of the adapter 5 and the PLG 81 of the endoscope 2, special light observation can be performed by irradiating a subject with a special light also in the single-use endoscope 2.

Figure 16:
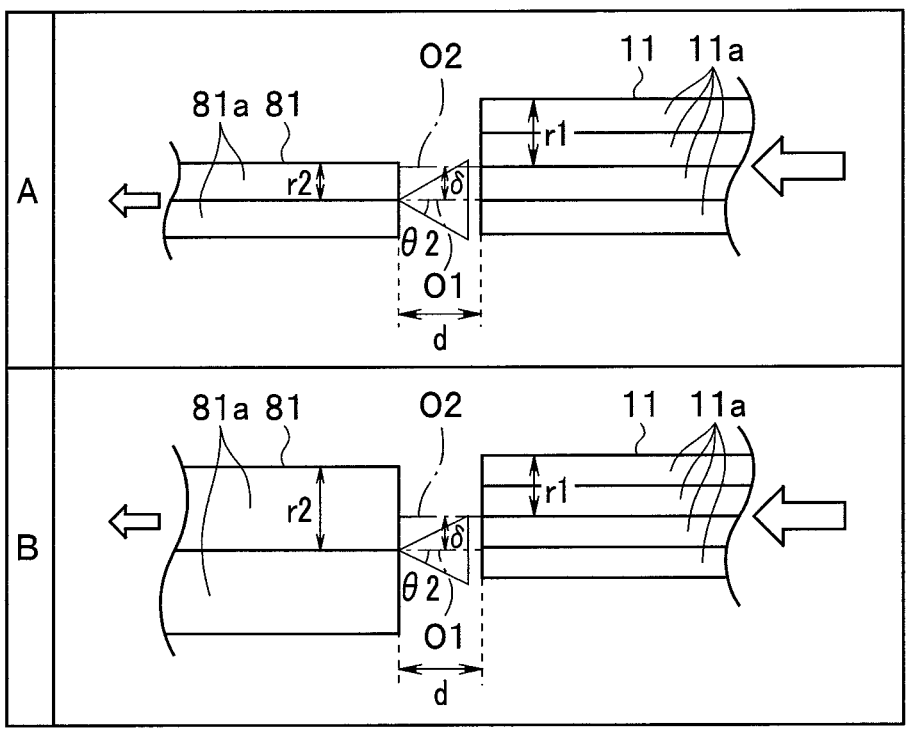
FIG. 16 is a table for description of a configuration of suppressing variations in the transmission efficiency of illumination light from the glass LG to the PLG in the aforementioned seventh embodiment.

FIG. 16 is a table for description of a configuration of suppressing variations in the transmission efficiency of illumination light from the glass LG 11 to the PLG 81 in the seventh embodiment.

When the light guide connector 82 and the light guide receiver 12 are connected, the glass LG 11 and the PLG 81 abut against each other. At this time, the disparity in the eccentricity in the direction perpendicular to the optical axis 02 of the glass LG 11 and the optical axis 01 of the PLG 81 is δ as described above. The maximum value of the variation in the distance between the glass LG 11 and the PLG 81 in the direction of the optical axes 01 and 02 is represented as d. The radius of the glass LG 11 is represented as r1, the radius of the PLG 81 is represented as r2, and the numerical aperture (NA) of the PLG 81 is represented as $\sin\theta2$. Note that the exact numerical aperture is obtained by multiplying the $\sin\theta2$ by the refractive index n of a medium, but since the refractive index for air as a medium is roughly 1, and thus, the numerical aperture is simply represented as $\sin\theta2$.

At this time, the conditional expression to suppress the variations in the transmission efficiency of the illumination light from the glass LG 11 to the PLG 81 due to the disparity in the eccentricity δ is defined by the following expression (1):

$$\delta \leq d \times \tan(\theta2) - (r1 - r2). \tag{1}$$

Column A of FIG. 16 shows an example of r1≥r2. In this case, the second term on the right-hand side in the expression (1) becomes a negative value, and the limitation relative to the disparity in the eccentricity δ increases.

Meanwhile, column B of FIG. 16 shows an example of r1<r2. In this case, the second term on the right-hand side in the expression (1) becomes a positive value, and the limitation relative to the disparity in the eccentricity δ is relaxed. In this manner, when r2 is increased, the improvement in the transmission efficiency of the illumination light can be expected. However, simply increasing r2 makes the PLG 81 thicker, and accordingly increases the diameter of the insertion portion 2a of the endoscope 2. Therefore, the radius r2 of the PLG 81 can be set small as much as possible by properly adjusting each parameter so as to satisfy the expression (1).

FIG. 17 is a table for description of some examples of the glass LG 11 and the PLG 81 in the seventh embodiment.

Column A of FIG. 17 shows a first example. The first example is an example in which the PLG 81 is configured with two strands 81a. The numerical data of the first example is as follows.

| | |
|---|---|
| Diameter of strand 11a of glass LG 11 | 0.03 mm |
| Diameter of strand 81a of PLG 81 | 0.5 mm |
| Numerical aperture of glass LG 11 | 0.6 |
| Numerical aperture of PLG 81 | 0.5 |
| The number of strands 11a of glass LG 11 | 1500 |
| The number of strands 81a of PLG 81 | 2 |
| r1 | 0.58 mm |
| r2 | 0.50 mm |
| d | 0.3 mm |
| θ1 | 37° |
| θ2 | 30° |
| δ_max | 0.1 mm |

Column B of FIG. 17 shows a second example. The second example is an example in which the PLG 81 is configured with four strands 81a. The numerical data of the second example is as follows.

| | |
|---|---|
| Diameter of strand 11a of glass LG 11 | 0.03 mm |
| Diameter of strand 81a of PLG 81 | 0.5 mm |
| Numerical aperture of glass LG 11 | 0.6 |
| Numerical aperture of PLG 81 | 0.5 |
| The number of strands 11a of glass LG 11 | 1500 |
| *The number of strands 81a of PLG 81 | 4 |
| r1 | 0.58 mm |
| *r2 | 0.60 mm |
| d | 0.3 mm |
| θ1 | 37° |
| θ2 | 30° |
| *δ_max | 0.2 mm |

Column C of FIG. 17 shows a third example. The third example is an example in which the PLG 81 is configured with seven strands 81a. The numerical data of the third example is as follows.

| | |
|---|---|
| Diameter of strand 11a of glass LG 11 | 0.03 mm |
| Diameter of strand 81a of PLG 81 | 0.5 mm |
| Numerical aperture of glass LG 11 | 0.6 |
| Numerical aperture of PLG 81 | 0.5 |
| The number of strands 11a of glass LG 11 | 1500 |
| *The number of strands 81a of PLG 81 | 7 |
| r1 | 0.58 mm |
| *r2 | 0.75 mm |
| d | 0.3 mm |
| θ1 | 37° |
| θ2 | 30° |
| *δ_max | 0.3 mm |

For easy comparison among the examples, a symbol "*" is attached to portions of the second and the third examples that are different from the first example. In the examples, the configuration of the glass LG of FIG. 17 is the same. Note that numerical aperture of the glass LG 11 is represented as $\sin\theta1$.

Figure 18:
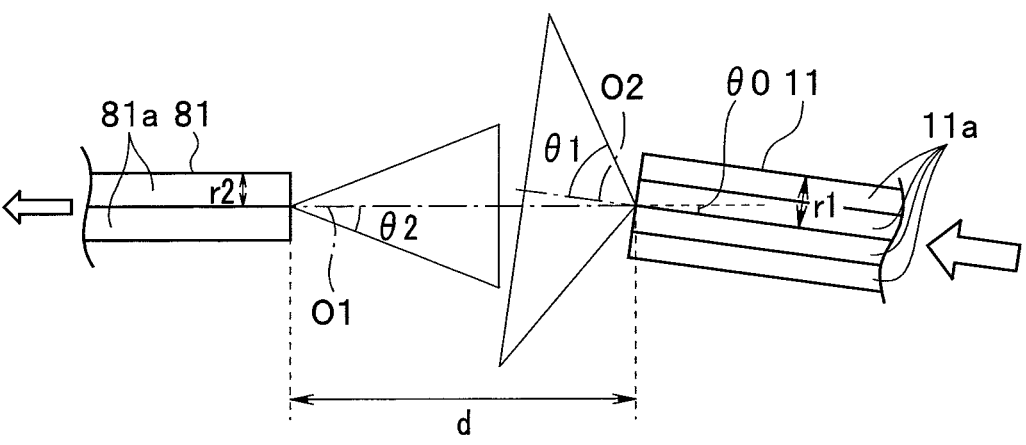
FIG. 18 is a diagram for description of a configuration of suppressing variations in the transmission efficiency of illumination light in a case where an optical axis of the glass LG is tilted relative to an optical axis of the PLG in the aforementioned seventh embodiment.

FIG. 18 is a diagram for description of a configuration of suppressing variations in the transmission efficiency of illumination light in a case where the optical axis 02 of the glass LG 11 is tilted relative to the optical axis 01 of the PLG 81 in the seventh embodiment.

A value 00 is set as the maximum tilt angle of the optical axis 02 relative to the optical axis 01 when the light guide connector 82 and the light guide receiver 12 are connected. When an expression (2) below is satisfied, an expression (3) below is the conditional expression to suppress the variations in the transmission efficiency of the illumination light from the glass LG 11 to the PLG 81, with d as the maximum value of the distance between the glass LG 11 and the PLG 81 in the direction of the optical axes 01 and 02 and the maximum tilt angle θ0:

$$\theta 1 > (\theta 2 + \theta 0) \qquad (2)$$

$$r1 > r2 + d \times \tan(\theta 2 + \theta 0). \qquad (3)$$

Therefore, it is recommended that the glass LG 11, the PLG 81, the light guide connector 82, the light guide receiver 12, and the like should be designed so as to satisfy the expressions (1) to (3).

According to such a seventh embodiment, substantially the same advantageous effects as the advantageous effects of the aforementioned first to sixth embodiments are produced.

According to the seventh embodiment, the variations in the transmission efficiency of illumination light from the glass LG 11 to the PLG 81 can be suppressed, so as to enable to reduce the loss of the illumination light.

Eighth Embodiment

Figure 19:
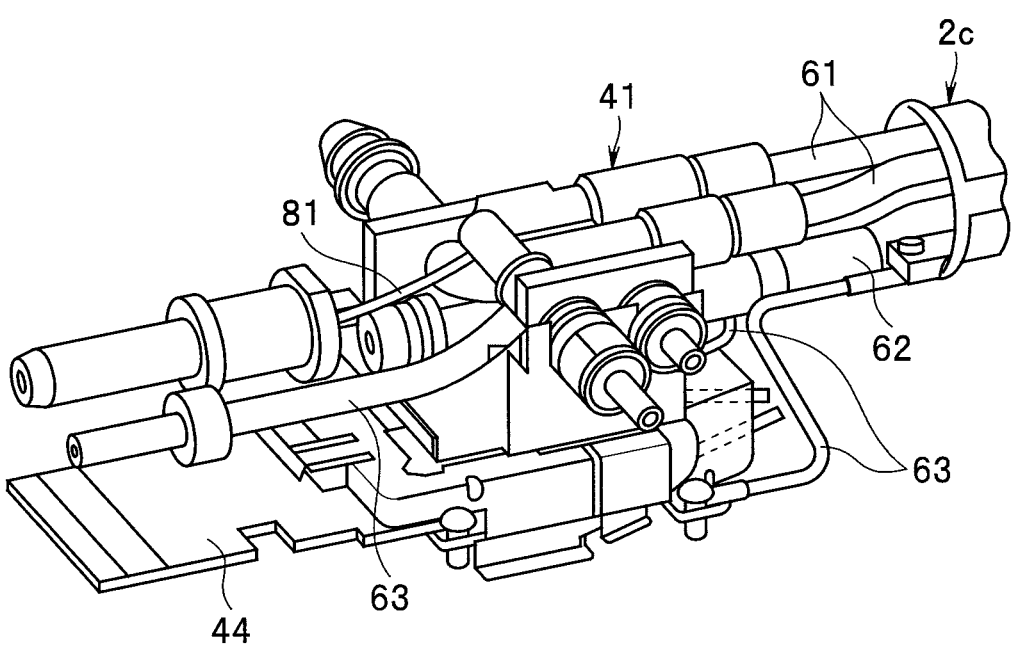
FIG. 19 is a perspective view showing an internal configuration of a connector of the endoscope in an eighth embodiment of the present disclosure.
Figure 20:
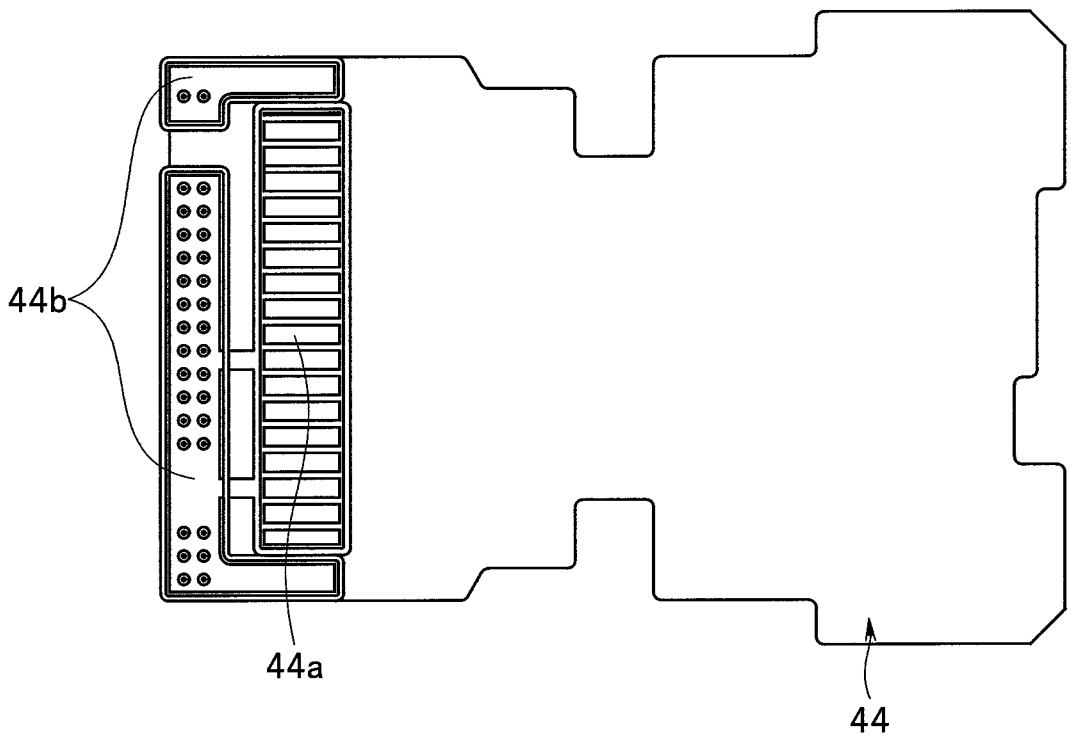
FIG. 20 is a plan view showing a configuration of the electric circuit board in the aforementioned eighth embodiment.

FIG. 19 and FIG. 20 show an eighth embodiment of the present disclosure. FIG. 19 is a perspective view showing an internal configuration of the connector 2cl of the endoscope 2 in the eighth embodiment. In the eighth embodiment, the same portions as the portions of the first to seventh embodiments are assigned the same reference numerals and the descriptions are omitted, as appropriate. In the eighth embodiment, the points different from the first to seventh embodiments will mainly be described.

A conduit 61 of the air and water feeding channel, a conduit 62 of the suction channel, a signal wire 63, the PLG 81, and the like are disposed inside the universal cable 2c.

The connector 2cl of the endoscope 2 includes a connector main body 41 to which the conduit 61 of the air and water feeding channel, the conduit 62 of the suction channel, the signal wire 63, the PLG 81, and the like are connected, and a connector cover having a mechanism for detachable connection to the connector receiver 5b of the adapter 5. The connector cover covers the surrounding of the distal end side of the connector main body 41.

The connector cover includes the lightning arresting structural part for protection from the static electricity. The lightning arresting structural part is provided in a position that covers an electric circuit board 44 of the connector main body 41. The electric circuit board 44 is disposed in an end portion on the lower face side of the connector main body 41, for example.

FIG. 20 is a plan view showing a configuration of the electric circuit board 44 in the eighth embodiment.

In the electric circuit board 44 shown in FIG. 20, print wiring is formed and an electric component is mounted so as to connect the print wiring (illustrations of the print wiring and the electric component are omitted). Note that as described above, the electric circuit board 44 is not provided with a circuit that converts the format of a video signal. Thus, downsizing and cost reduction of the electric circuit board 44 can be realized. The insertion instrument comprises a third connector connected to the second connector. The third connector includes an electric contact that transmits an electric signal and power, and a contact for grounding located around the electric contact and connected to a grounding circuit of the processor via the relay adapter.

One end side of the electric circuit board 44 is provided with a signal pad 44a. A plurality of electric contacts are arranged on the signal pad 44a. The plurality of electric contacts are connected to the signal wire 63 and transmit an electric signal including power. A ground pad 44b (contact for grounding) is provided in the surrounding of the signal pad 44a, in other words, so as to cover the edge of the electric circuit board 44 on the outer peripheral side of the signal pad 44a.

In the state in which the connector main body 41 and the connector cover are assembled, the lightning arresting structural part is electrically connected to the ground pad 44b. At this time, the signal pad 44a is surrounded by the lightning arresting structural part and the ground pad 44b in an opening on the side that is connected to the connector receiver 5b. The signal pad 44a is disposed in the rear inside the connector 2cl, and the ground pad 44b and the lightning arresting structural part are disposed on the side exposed to the outside.

The lightning arresting structural part and the ground pad 44b are connected to a grounding circuit of the video processor 3 via the adapter 5.

According to such an eighth embodiment, substantially the same advantageous effects as the advantageous effects of the aforementioned first to seventh embodiments are produced.

According to the eighth embodiment, the signal pad 44a is disposed in the rear inside the connector 2cl, and the ground pad 44b and the lightning arresting structural part are disposed on the side exposed to the outside, so that the effect of the static electricity on the image sensor 21 via the signal pad 44a can be prevented.

In the aforementioned descriptions, the endoscope, specifically the reusable endoscope 2A and the single-use endoscope 2 are provided as the examples of the insertion instrument, but the insertion instrument is not limited to the examples. For example, the insertion instrument may be a treatment instrument, an ultrasound probe, or the like.

In the aforementioned descriptions, the endoscope system 1 using the endoscope is provided as the example of the insertion instrument system, but the insertion instrument system may also use an insertion instrument other than the endoscope.

The present invention is not limited to the exactly the same embodiments described above. The present invention may be embodied by modifying the constituent elements within the scope without departing from the gist of the invention in the implementing stage. The various aspects of the invention may be formed by appropriately combining a plurality of constituent elements disclosed in the aforementioned embodiments. For example, some constituent elements may be deleted from all the constituent elements disclosed in the embodiments. The constituent elements of different embodiments may also be combined as appropriate. In this manner, it goes without saying that various modifications and applications are available within the scope without departing from the gist of the invention.

Example 1. A relay adapter configured to link a processor and an insertion instrument, the relay adapter comprising:

a first connector connected to the processor;

a second connector connected to the insertion instrument;

a power circuit configured to convert power supplied from the processor into power corresponding to the insertion instrument and to supply, to the insertion instrument, the power converted; and a switching circuit configured to cause the power circuit to shut off supplying the power to the insertion instrument when the first connector and the processor are connected and the second connector and the insertion instrument are not connected.

Example 2. The relay adapter according to Example 1, wherein the switching circuit is configured to cause the power circuit to supply the power to the insertion instrument when the first connector and the processor are connected and the second connector and the insertion instrument are connected.

Example 3. The relay adapter according to Example 2, further comprising a determination signal receiving circuit configured to receive a determination signal related to a model of the insertion instrument from the insertion instrument, wherein the switching circuit is configured to:

cause the power circuit to shut off supplying the power to the insertion instrument when the determination signal receiving circuit does not receive the determination signal; and cause the power circuit to supply the power to the insertion instrument when the determination signal receiving circuit receives the determination signal.

Example 4. The relay adapter according to Example 3, further comprising:

a video signal processing circuit configured to convert a video signal received from an image sensor included in the insertion instrument into a video signal in a signal format processable by the processor and to output, to the processor, the video signal converted, wherein the determination signal receiving circuit further receives a second determination signal related to a type of the image sensor included in the insertion instrument, and the video signal processing circuit converts the signal format of the video signal in accordance with the type of the image sensor determined from the second determination signal.

Example 5. The relay adapter according to Example 4, further comprising a first resistor unit, wherein the first resistor unit has a resistance value that is same as a resistance value of another resistor unit included in another insertion instrument that is connectable to the processor, the first resistor unit is connected to an insertion instrument determination circuit included in the processor, via the first connector, and the power circuit is configured to convert, on a basis of the resistance value of the first resistor unit, the power supplied from the processor, the power corresponding to the other insertion instrument determined by the insertion instrument determination circuit into power corresponding to the type of the image sensor determined from the second determination signal and to supply, to the insertion instrument, the power converted.

Example 6. The relay adapter according to Example 4, wherein the determination signal is a signal indicating the model of the insertion instrument, the second determination signal is a signal indicating the type of the image sensor, and the determination signal and the second determination signal are received from a memory included in the insertion instrument.

Example 7. The relay adapter according to Example 4, wherein the determination signal is received from a second resistor unit having a second resistance value, the second resistor unit being included in the insertion instrument, the second determination signal is received from a third resistor unit having a third resistance value, the third resistor unit being included in the insertion instrument, a memory is further included, the memory retaining first information indicating a relation between the second resistance value and the model of the insertion instrument and second information indicating a relation between the third resistance value and the type of the image sensor, and the determination signal receiving circuit is configured to determine the model of the insertion instrument on a basis of the determination signal and the first information and to determine the type of the image sensor on a basis of the second determination signal and the second information.

Example 8. The relay adapter according to Example 1, further comprising:

first wiring; and second wiring, wherein one end of the first wiring is connected to a connection detection circuit included in the processor, via the first connector, another end of the first wiring is connected to one end of third wiring included in the insertion instrument, via the second connector, one end of the second wiring is grounded, and another end of the second wiring is connected to another end of the third wiring that loops inside the insertion instrument, via the second connector.

Example 9. The relay adapter according to Example 1, further comprising a light guide configured to take in illumination light supplied from a light source included in the processor, via the first connector and to guide and output the illumination light to the insertion instrument, via the second connector.

Example 10. The relay adapter according to Example 9, wherein the light guide comprises a glass fiber bundle in which a plurality of glass fibers are bundled.

Example 11. An insertion instrument system, comprising:

an insertion instrument configured to be inserted into a subject;

a processor configured to supply power to the insertion instrument and to receive an electric signal from the insertion instrument, and a relay adapter configured to link the processor and the insertion instrument, wherein the relay adapter includes:

a first connector connected to the processor;

a second connector connected to the insertion instrument;

a power circuit configured to convert the power supplied from the processor into power corresponding to the insertion instrument and to supply, to the insertion instrument, the power converted; and a switching circuit configured to cause the power circuit to shut off supplying the power to the insertion instrument when the first connector and the processor are connected and the second connector and the insertion instrument are not connected.

Example 12. The insertion instrument system according to Example 11, wherein the processor comprises a connection detection circuit, the relay adapter further comprises first wiring and second wiring, the insertion instrument comprises third wiring, one end of the first wiring is connected to the connection detection circuit, via the first connector, another end of the first wiring is connected to one end of the third wiring, via the second connector, one end of the second wiring is grounded, another end of the second wiring is connected to another end of the third wiring that loops inside the insertion instrument, via the second connector, the processor is configured to supply the power to the relay adapter when the connection detection circuit detects grounding, and the switching circuit is configured to cause the power circuit to supply the power to the insertion instrument when the first connector and the processor are connected and the second connector and the insertion instrument are connected.

Example 13. The insertion instrument system according to Example 12, wherein the relay adapter further comprises a determination signal receiving circuit configured to receive a determination signal related to a model of the insertion instrument from the insertion instrument, and the switching circuit is configured to:

cause the power circuit to shut off supplying the power to the insertion instrument when the determination signal receiving circuit does not receive the determination signal; and cause the power circuit to supply the power to the insertion instrument when the determination signal receiving circuit receives the determination signal.

Example 14. The insertion instrument system according to Example 13, wherein the relay adapter further comprises a first resistor unit, the first resistor unit has a resistance value that is same as a resistance value of another resistor unit included in another insertion instrument that is connectable to the processor, the first resistor unit is connected to an insertion instrument determination circuit included in the processor, via the first connector, the determination signal receiving circuit is configured to further receive a second determination signal related to a type of an image sensor included in the insertion instrument, and the power circuit is configured to convert, on a basis of the resistance value of the first resistor unit, the power supplied from the processor, the power corresponding to the other insertion instrument determined by the insertion instrument determination circuit into power corresponding to the type of the image sensor determined from the second determination signal and to supply, to the insertion instrument, the power converted.

Example 15. The insertion instrument system according to Example 13, wherein the power circuit of the relay adapter is configured to convert the power supplied from the processor into power corresponding to a standard insertion instrument including a cable having a first length and to supply the power converted, and the insertion instrument includes:

a cable having a second length configured to transmit the power supplied via the second connector; and an adjustment circuit configured to adjust a power difference due to a difference between the second length and the first length.

Example 16. The insertion instrument system according to Example 11, wherein the relay adapter further comprises a light guide configured to take in illumination light supplied from a light source included in the processor, via the first connector, and to guide and output the illumination light to the insertion instrument, via the second connector.

Example 17. The insertion instrument system according to Example 16, wherein the light guide comprises a glass fiber bundle in which a plurality of glass fibers are bundled, the insertion instrument comprises a second light guide configured to guide the illumination light taken in through the light guide, the second light guide comprises a resin fiber bundle in which a plurality of transparent resin fibers are bundled, and when a radius of the light guide is represented as r1, a radius of the second light guide is represented as r2, a numerical aperture of the second light guide is represented as $\sin\theta2$, a disparity in an eccentricity between the light guide and the second light guide abutting against each other is represented as $\delta$, and a maximum value of a variation in a distance between the light guide and the second light guide abutting against each other in an optical axis direction is represented as d, a relation defined by a following expression is satisfied:

$$\delta \leq d \times \tan(\theta2) - (r1 - r2)$$

Example 18. The insertion instrument system according to Example 11, wherein the insertion instrument comprises a third connector connected to the second connector and including an electric contact that transmits an electric signal including the power, and the third connector comprises a contact for grounding connected to a grounding circuit of the processor via the relay adapter, in a surrounding of the electric contact.

Example 19. The insertion instrument system according to Example 11, wherein the insertion instrument is an endoscope.

Example 20. The insertion instrument system according to Example 19, wherein the endoscope is a single-use endoscope that is disposed of after being used once.

What is claimed is:

1. A relay adapter, comprising:

a first connector configured to connect to a processor supplying a first power:

a second connector configured to connect to an insertion instrument operable using a second power;

a power circuit coupled to the first connector to receive the first power, configured to convert the first power into the second power, and coupled to the second connector for delivering the second power to the second connector;

a switching circuit coupled to the power circuit; and a determination signal receiving circuit coupled via the second connector to the insertion instrument to receive a first determination signal from the insertion instrument, configured to provide a first output corresponding to receiving the first determination signal and to provide a second output corresponding to not receiving the first determination signal, and coupled to the switching circuit to deliver the first output and the second output to the switching circuit, wherein, when the second connector is not connected to the insertion instrument, the switching circuit prevents the power circuit from delivering the second power to the second connector, wherein, when the first connector is connected to the processor and the second connector is connected to the insertion instrument, the switching circuit permits the power circuit to deliver the second power to the second connector, wherein the switching circuit is configured to:

operate the power circuit to deliver the second power to the second connector when the switching circuit receives the first output, and operate the power circuit to prevent delivery of the second power to the second connector when the switching circuit receives the second output, and wherein the first determination signal is related to a model of the insertion instrument.

2. The relay adapter according to claim 1, further comprising a video signal processing circuit coupled via the second connector to the insertion instrument to receive a second determination signal from the insertion instrument, configured to receive a first video signal from an image sensor included in the insertion instrument and to convert the first video signal into a second video signal in accordance with a type of the image sensor, and coupled to the processor to output the second video signal to the processor, wherein the second determination signal is related to the type of the image sensor.

3. The relay adapter according to claim 2, further comprising a first resistor unit having a first resistance value, wherein the first resistor unit is coupled via the first connector to an insertion instrument determination circuit included in the processor and the first resistor unit is configured to generate a voltage value corresponding to the type of the image sensor, and wherein the second power corresponds to the voltage value.

4. The relay adapter according to claim 2, wherein the first determination signal and the second determination signal are generated from a memory included in the insertion instrument.

5. The relay adapter according to claim 2, wherein the first determination signal is generated from a first resistor unit included in the insertion instrument, wherein the second determination signal is generated from a second resistor unit included in the insertion instrument, wherein the first resistor unit has a first resistance value, and the second resistor unit has a second resistance value, wherein the relay adapter further comprises a memory configured to retain a first information and a second information, the first information indicating a relation between the first resistance value and the model of the insertion instrument, and the second information indicating a relation between the second resistance value and the type of the image sensor, and wherein the determination signal receiving circuit is further configured to determine the model of the insertion instrument based on the first determination signal and the first information, and the determination signal receiving circuit is further configured to determine the type of the image sensor based on the second determination signal and the second information.

6. A relay adapter, comprising:

a first connector configured to connect to a processor supplying a first power:

a second connector configured to connect to an insertion instrument operable using a second power;

a power circuit coupled to the first connector to receive the first power, configured to convert the first power into the second power, and coupled to the second connector for delivering the second power to the second connector:

a switching circuit coupled to the power circuit;

a first wiring including a first end and a second end; and a second wiring including a third end and a fourth end, wherein, when the second connector is not connected to the insertion instrument, the switching circuit prevents the power circuit from delivering the second power to the second connector, wherein the first end of the first wiring is connected to the first connector, wherein the second end of the first wiring is connected to the second connector, wherein the third end of the second wiring is grounded, and wherein the fourth end of the second wiring is connected to the second connector.

7. A relay adapter, comprising:

a first connector configured to connect to a processor supplying a first power;

a second connector configured to connect to an insertion instrument operable using a second power;

a power circuit coupled to the first connector to receive the first power configured to convert the first power into the second power, and coupled to the second connector for delivering the second power to the second connector;

a switching circuit coupled to the power circuit; and a light guide having a first end and a second end, wherein, when the second connector is not connected to the insertion instrument, the switching circuit prevents the power circuit from delivering the second power to the second connector, wherein the light guide is configured to receive at the first end an illumination light from a light source received via the first connector and guide the received illumination light to the second end, and deliver guided illumination light to the second connector.

8. The relay adapter according to claim 7, wherein the light guide comprises a glass fiber bundle.

9. An insertion instrument system, comprising:

an insertion instrument configured to be inserted into a subject; and a relay adapter, wherein the relay adapter includes:

a first connector configured to connect to a processor supplying a first power, a second connector configured to connect to the insertion instrument, the insertion instrument operable using a second power, a power circuit coupled to the first connector to receive the first power configured to convert the first power into the second power, and coupled to the second connector for delivering the second power to the insertion instrument via the second connector, a switching circuit coupled to the power circuit, a first wiring including a first end and a second end, and a second wiring including a third end and a fourth end, and wherein, when the second connector is not connected to the insertion instrument, the switching circuit prevents the power circuit from delivering the second power to the second connector, wherein the insertion instrument comprises a third wiring that loops inside the insertion instrument and includes a fifth end and a sixth end, wherein the first end of the first wiring is connected via the first connector to a connection detection circuit included in the processor, wherein the second end of the first wiring is connected via the second connector to the fifth end of the third wiring, wherein the third end of the second wiring is grounded, wherein the fourth end of the second wiring is connected via the second connector to the sixth end of the third wiring, and wherein, when the first connector is connected to the processor and the second connector is connected to the insertion instrument, the switching circuit permits the power circuit to deliver the second power to the second connector.

10. An insertion instrument system, comprising:

an insertion instrument configured to be inserted into a subject; and a relay adapter, wherein the relay adapter includes:

a first connector configured to connect to a processor supplying a first power, a second connector configured to connect to the insertion instrument, the insertion instrument operable using a second power, a power circuit coupled to the first connector to receive the first power, configured to convert the first power into the second power, and coupled to the second connector for delivering the second power to the insertion instrument via the second connector, a switching circuit coupled to the power circuit, and a determination signal receiving circuit coupled via the second connector to the insertion instrument to receive a first determination signal from the insertion instrument, configured to provide a first output corresponding to receiving the first determination signal and to provide a second output corresponding to not receiving the first determination signal, and coupled to the switching circuit to deliver the first output and the second output to the switching circuit, and wherein, when the second connector is not connected to the insertion instrument, the switching circuit prevents the power circuit from delivering the second power to the second connector, wherein the switching circuit is configured to:

operate the power circuit to deliver the second power to the second connector when the switching circuit receives the first output, and operate the power circuit to prevent delivery of the second power to the second connector when the switching circuit receives the second output, and wherein the first determination signal is related to a model of the insertion instrument.

11. The insertion instrument system according to claim 10, wherein the insertion instrument includes an image sensor, wherein the relay adapter further comprises a first resistor unit having a first resistance value, wherein the first resistor unit is coupled via the first connector to an insertion instrument determination circuit included in the processor and the first resistor unit is configured to generate a voltage value corresponding to a type of the image sensor, wherein the second power corresponds to the voltage value, and wherein the determination signal receiving circuit is further configured to receive a second determination signal related to the type of the image sensor.

12. The insertion instrument system according to claim 10, wherein the insertion instrument includes:

a cable having a length sufficient to transmit the first power to the second power via the second connector, and an adjustment circuit configured to adjust the second power based on the length of the cable.

13. An insertion instrument system, comprising:

an insertion instrument configured to be inserted into a subject; and a relay adapter, wherein the relay adapter includes:

a first connector configured to connect to a processor supplying a first power, a second connector configured to connect to the insertion instrument, the insertion instrument operable using a second power, a power circuit coupled to the first connector to receive the first power, configured to convert the first power into the second power, and coupled to the second connector for delivering the second power to the insertion instrument via the second connector, a switching circuit coupled to the power circuit, and a light guide having a first end and a second end, and wherein, when the second connector is not connected to the insertion instrument, the switching circuit prevents the power circuit from delivering the second power to the second connector, wherein the light guide is configured to receive at the first end an illumination light from a light source received via the first connector and guide the received illumination light to the second end, and deliver guided illumination light to the insertion instrument via the second connector.

14. The insertion instrument system according to claim 13, wherein the first light guide comprises a glass fiber bundle, wherein the insertion instrument includes a second light guide comprising a resin fiber bundle, wherein the second light guide is configured to guide the received illumination light, and wherein a relation defined by a following expression is satisfied:

$$\delta \le d \times \tan(\theta 2) - (r1 - r2)$$

where: a radius of the first light guide is represented as r1, a radius of the second light guide is represented as r2, a numerical aperture of the second light guide is represented as $\sin\theta 2$, a disparity in an eccentricity between the first light guide and the second light guide abutting against each other is represented as $\delta$, and a maximum value of a variation in a distance between the first light guide and the second light guide abutting against each other in an optical axis direction is represented as d.

15. An insertion instrument system, comprising:

an insertion instrument configured to be inserted into a subject; and a relay adapter, wherein the relay adapter includes:

a first connector configured to connect to a processor supplying a first power;

a second connector configured to connect to the insertion instrument, the insertion instrument operable using a second power;

a power circuit coupled to the first connector to receive the first power, configured to convert the first power into the second power, and coupled to the second connector for delivering the second power to the insertion instrument via the second connector; and a switching circuit coupled to the power circuit, and wherein, when the second connector is not connected to the insertion instrument the switching circuit prevents the power circuit from delivering the second power to the second connector, wherein the insertion instrument comprises a third connector connected to the second connector, and wherein the third connector includes:

an electric contact that transmits an electric signal and power, and a contact for grounding located around the electric contact and connected to a grounding circuit of the processor via the relay adapter.

16. The insertion instrument system according to claim 13, wherein the insertion instrument is an endoscope.

17. The insertion instrument system according to claim 16, wherein the endoscope is a single-use endoscope.

* * * * *